United States Patent
Collin et al.

(10) Patent No.: US 9,707,279 B2
(45) Date of Patent: Jul. 18, 2017

(54) TREATMENT FOR IGE-MEDIATED DISEASE

(75) Inventors: Mattias Collin, Lund (SE); Rolf Lood, New York, NY (US); Karl Carlstrom, Hok (SE); Maria Allhorn, Ramlosa (SE); Jonathan Sjogren, Lund (SE); Falk Nimmerjahn, Erlangen (DE)

(73) Assignee: Hansa Medical AB, Lund (SE)

( * ) Notice: Subject to any disclaimer, the term of this patent is extended or adjusted under 35 U.S.C. 154(b) by 231 days.

(21) Appl. No.: 14/002,949

(22) PCT Filed: Mar. 5, 2012

(86) PCT No.: PCT/EP2012/053747
§ 371 (c)(1),
(2), (4) Date: Nov. 18, 2013

(87) PCT Pub. No.: WO2012/119983
PCT Pub. Date: Sep. 13, 2012

(65) Prior Publication Data
US 2014/0065128 A1    Mar. 6, 2014

(30) Foreign Application Priority Data
Mar. 4, 2011 (GB) .................................. 1103780.1

(51) Int. Cl.
A61K 38/47 (2006.01)
G01N 33/68 (2006.01)
A61K 31/7088 (2006.01)
A61K 35/14 (2015.01)

(52) U.S. Cl.
CPC .......... *A61K 38/47* (2013.01); *A61K 31/7088* (2013.01); *A61K 35/14* (2013.01); *G01N 33/6854* (2013.01); *G01N 2500/00* (2013.01)

(58) Field of Classification Search
None
See application file for complete search history.

(56) References Cited

FOREIGN PATENT DOCUMENTS

| WO | 03/051914 A2 | 6/2003 |
| WO | 2008/071418 A2 | 6/2008 |
| WO | 2009/033670 A2 | 3/2009 |
| WO | 2010/057626 A1 | 5/2010 |

OTHER PUBLICATIONS

C. Suphioglu et al. "Molecular basis of IgE recognition of Lol p 5 a major allergen of rye grass pollen", Molecular Immunology 35: 293-205. (1998).*
J.E.M. Bjorklund et al. "N-Glycosylation Influences Epitope Expression and Receptor Binding Structures in Human IgE", Molecular Immunology 36: 213-221. (1999).*
Y. Matsuda et al. "Another Ant-Allergic Mechanism: Antibody IgE Deglycosylation Induced by a Substance Extracted From Human Urine", Yale J. biol. Medicine 74:145-149 (2001).*
I. Syers et al. "Amino Acid Residues That Influence Fc-epsilon-RI-Mediated Effector Functions of Human Immunoglobulin E", Biochemistry 37:16152-16164. (1998).*
A. Taylor et al. "The Crystal Structure of an Avian IgY-Fc Fragment Reveals Conservation with both Mammalian IgG and IgE", Biochemistry 48:558-562 (2009).*
Albert et al., "In vivo enzymatic modulation of IgG glycosylation inhibits autoimmune disease in an IgG subclass-dependent manner," *PNAS* 105(39):15005-15009, 2008.
Arnold et al., "The Glycosylation of Human Serum IgD and IgE and the Accessibility of Identified Oligomannose Structures for Interaction with Mannan-Binding Lectin," *The Journal of Immunology* 173:6831-6840, 2004.
Baruah et al., "Selective Deactivation of Serum IgG: A General Strategy for the Enhancement of Monoclonal Antibody Receptor Interactions," *Journal of Molecular Biology* 420:1-7, 2012.
Collin et al., "EndoS, a novel secreted protein from *Streptococcus pyogenes* with endoglycosidase activity on human IgG," *The EMBO Journal* 20(12):3046-3055, 2001.
Collin et al., "Effect of SpeB and EndoS from *Streptococcus pyogenes* on Human Immunoglobulins," *Infection and Immunity* 69(11):7187-7189, 2001.
Dorrington et al., "Structure-Function Relationships in Human Immunoglobulin E," *Immunological Rev.* 41:3-25, 1978.
Huber et al., "Crystallographic structure studies of an IgG molecule and an Fc fragment," *Nature* 264:415-420, 1976.
Nandakumar et al., "Therapeutic cleavage of IgG: new avenues for treating inflammation," *Trends in Immunology* 29(4):173-178, 2008.
Parekh et al., "Association of rheumatoid arthritis and primary osteoarthritis with changes in the glycosylation pattern of total serum IgG," *Nature* 316:452-457, 1985.
Rudd et al., "Glycosylation: Heterogeneity and the 3D Structure of Proteins," *Critical Reviews in Biochemistry and Molecular Biology* 32(1):1-100, 1997.
Wan et al., "The crystal structure of IgE Fc reveals an asymmetrically bent conformation," *Nature Immunology* 3(7):681-686, 2002.
Wurzburg et al., "Structure of the Human IgE-Fc Cε3-Cε4 Reveals Conformational Flexibility in the Antibody Effector Domains," *Immunity* 13:375-385, 2000.

* cited by examiner

*Primary Examiner* — Rebecca Prouty
(74) *Attorney, Agent, or Firm* — Seed IP Law Group LLP

(57) ABSTRACT

The invention provides an EndoS polypeptide, or a polynucleotide encoding an EndoS polypeptide, for use in a method for treating or preventing a disease or condition mediated by IgE antibodies.

6 Claims, 11 Drawing Sheets

A.

B.

TREATMENT FOR IGE-MEDIATED DISEASE

FIELD OF THE INVENTION

The present invention relates to a method for treating or preventing diseases or conditions mediated by IgE antibodies, such as allergy.

BACKGROUND OF THE INVENTION

IgE is a heterotetramer composed of two heavy chains and two light chains held together by disulfide bonds forming three regions separated by a protease sensitive section. The two identical Fab regions bind antigens and the single Fc region is responsible for effector functions, including binding to FCC receptors. The overall structure is similar to IgG, except that there is an additional C domain (Cε4) in the ε heavy chain of IgE relative to the γ heavy chain of IgG.

Both IgE and IgG are N-glycosylated. However, IgG has only one N-linked glycan at position Asn-297 of the γ-chain. Human IgE has seven N-linked glycans attached to the heavy ε-chain at different sites. The overall structures of IgG and IgE are shown in FIG. 1. Glycosylation sites are also indicated.

The detailed structure and composition of the glycans on IgE are not known, but the most common structure contains two N-acetylglucosamine (GlcNAc) residues in the base and a high density of mannose residues. Several glycans are located in the Fc-region of IgE; Asn-265 in the Cε2 domain, and Asn-371 and Asn-394 in the Cε3 domain. In addition, IgE from non-myeloma can have a further glycan at Asn-383 in the Cε3 domain The Asn-297-linked-glycan on IgG is of the complex biantennary type with a core fucose linked to the innermost GlcNAc. The glycan of each γ heavy chain is located in the interface between the Cγ2 domains (second constant domain of the γ heavy chains). Sequence alignment between IgG, IgD and IgE shows that the Asn-297 region on IgG is completely conserved in all three immunoglobulins, and may have a conserved role in folding, post-translational modification and function. Asn-265 in the Cε2 domain of IgE corresponds to Asn-297 of IgG.

EndoS is an endoglycosidase secreted by the human pathogen *Streptococcus pyogenes*. EndoS was identified as an enzyme which specifically hydrolyzes the Asn-297-linked glycan on IgG between the two core GlcNAc residues. In contrast to many related endoglycosidases that require or are enhanced by denaturation of the glycoprotein substrate, EndoS specifically hydrolyzes native IgG. No other substrate for EndoS has been reported.

SUMMARY OF THE INVENTION

The present inventors have shown that EndoS is able to directly interact with IgE with high affinity, and hydrolyzes at least one glycan in the Cε3 domain. The inventors have further demonstrated that the action of EndoS on IgE has functional consequences, including inhibiting the activation of FcεR bearing cells such as basophils or mast cells. Thus, EndoS is useful in treating and preventing diseases mediated by IgE antibodies.

In accordance with the present invention, there is thus provided a composition comprising an EndoS polypeptide or a polynucleotide encoding an EndoS polypeptide, for use in a method for treating or preventing a disease or condition mediated by IgE antibodies.

The present invention also provides:
a composition comprising an EndoS peptide or a polynucleotide encoding an EndoS polypeptide, for use in the manufacture of a medicament for treating or preventing a disease or condition mediated by IgE antibodies;
a method for treating or preventing a disease or condition mediated by IgE antibodies in a subject, the method comprising administering to the subject a therapeutically effective amount of an EndoS polypeptide, or a polynucleotide encoding an EndoS polypeptide;
a method for treating, ex vivo, blood taken from a patient suffering from a disease or condition mediated by IgE antibodies, comprising contacting the blood with an EndoS polypeptide;
a method of screening for a polypeptide which has greater:
(i) affinity (lower $K_D$) for IgE; and/or
(ii) IgE endoglycosidase activity; and/or
(iii) ability to remove IgE from the surface of a basophil or a mast cell; and/or
(iv) ability to reduce the activity of IgE in vivo;
when compared to a polypeptide consisting of the amino acid sequence of SEQ ID NO: 1, said method comprising:
(a) assessing the polypeptide for a characteristic of (i) to (iv) above; and
(b) comparing the results obtained in step (a) to the results obtained when assessing a polypeptide consisting of the amino acid sequence of SEQ ID NO: 1 for the same characteristic; and
a method for removing at least one glycan from an IgE molecule, said method comprising contacting an IgE-containing sample with an EndoS polypeptide.

BRIEF DESCRIPTION OF THE FIGURES

FIG. 8B shows the quantification of edema size in PBS (control) versus EndoS (treatment) animals. FIG. 8C shows the results of histology of ear tissue sections stained with toluidine blue to detect mast cells. FIG. 8D shows the quantification of dermal mast cell numbers present in 250 μm of ear skin; FIG. 8E shows the detection of EndoS in ear tissue with an EndoS specific polyclonal antibody followed by staining with an HRP coupled secondary antibody. As a control ear tissue of EndoS injected mice was only stained with the secondary HRP coupled antibody (EndoS control). Pictures were taken at a 100× magnification unless otherwise indicated. Scale bar represents 50 μm. Students t-test was used to evaluate statistical significance and a p-value <0.05 (*) was considered significant.

FIG. 9 shows the quantification of further experiments carried out as in FIG. 7. Both PNGaseF and EndoS treatment of IgE resulted in a highly significant reduction in the capacity of IgE to indue edema. Students t-test was used to evaluate statistical significance and a p-value <0.05 was considered significant. **p<0.01.

BRIEF DESCRIPTION OF THE SEQUENCES

Figure 1:
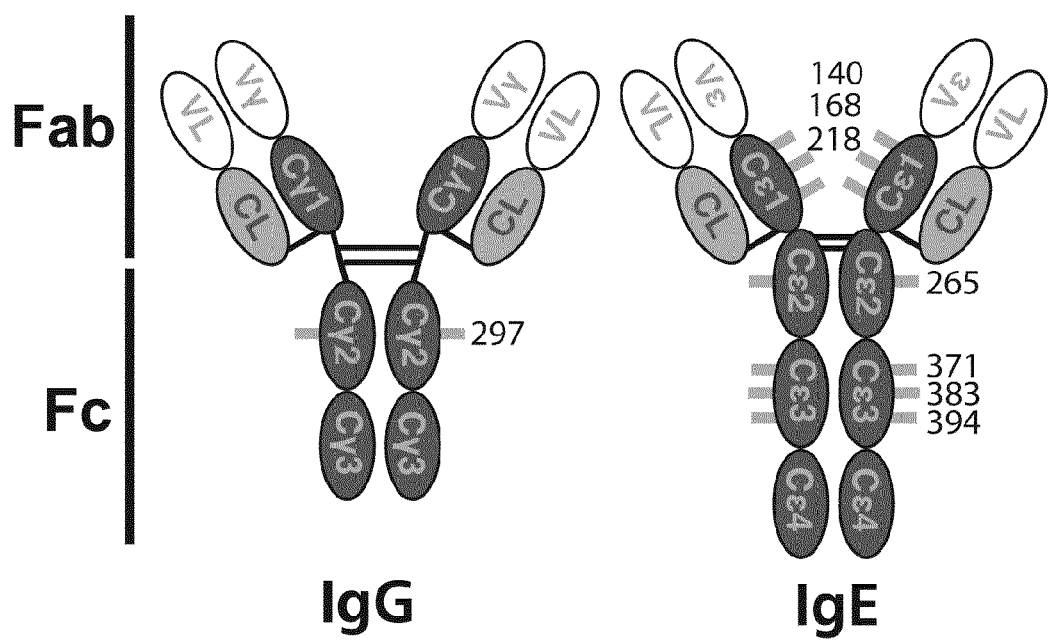
FIG. 1. Schematic representation of IgG and IgE structures and N-linked glycosylation. IgG has one N-linked glycan attached to Asn-297 situated on the constant portion of the γ-chain. Human IgE is heavily glycosylated along the E-chain.

SEQ ID NO: 1 is an amino acid sequence of EndoS isolated from *S. pyogenes* AP1.
SEQ ID NO: 2 is an amino acid sequence of EndoS isolated from *S. pyogenes* AP1, including a signal sequence.
SEQ ID NO: 3 is a nucleic acid sequence encoding EndoS isolated from *S. pyogenes* AP1, including a signal sequence.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polypeptide" includes "polypeptides", reference to "a polynucleotide" includes "polynucleotides", reference to "a substitution" includes two or more such substitutions, reference to "a variant" includes two or more such variants, reference to "a fragment" includes two or more such fragments, and the like.

All publications, patents and patent applications cited herein, whether supra or infra, are hereby incorporated by reference in their entirety.

IgE/Receptor-Interactions

IgE interacts with several receptors, mainly with the high-affinity receptor FcεRI, expressed predominantly on mast cells and basophils, but also on Langerhans cells and eosinophils. It also binds with low affinity to FcεRII/CD23, expressed on mature B-cells, activated macrophages, eosinophils, platelets and follicular dendritic cells. CD23 can also be expressed on several other cell types in the presence of interleukin-4 (IL-4). IgE is not restricted to its own Fcε-receptors, it can also interact with the Fcγ-receptors; FcγRIIb and FcγRIII, normally interacting with low affinity relative to IgG.

The high-affinity IgE receptor, FcεRI, consists of the IgE binding α-subunit, the intracellular β-subunit and two γ-subunits (αβγ2). Both human mast cells and basophils express this tetramer, but murine mast cells only express a trimer (αγ2), lacking the β-subunit. The density of FcεRI on the surface of human basophils can show a great variation between atopic and non-atopic individuals, ranging between 100,000-250,000 receptors/cell.

The FcεRI receptor binds to IgE with extremely high affinity and conformational changes in each of the Cε2, Cε3 and Cε4 domains appear to be necessary for this unique IgE/receptor interaction. Accordingly it has not previously been possible to identify the specific glycans on IgE which play a role in the IgE/receptor interaction, or even the domain to which such glycans are attached. The glycan attached to Asn-265 in the Cε2 domain has been viewed as the most obvious candidate by analogy with the glycan attached to Asn-297 on IgG.

The present inventors have now shown that the glycans in the Cε3 domain are important. As demonstrated herein, EndoS is able to directly interact with IgE with high affinity, and hydrolyzes at least one glycan in the Cε3 domain. The present inventors have found that EndoS from *S. pyogenes* hydrolyzes IgE glycans in solution and in human blood and in vivo in mice. The inventors have further shown that deglycosylation of IgE by EndoS abrogates its functional effects in vitro and in vivo. In particular, effects mediated by the interaction between IgE and FcεRI are reduced. For example, EndoS treatment of IgE in human blood led to the inhibition of IgE-mediated basophil activation. In addition, IgE treated with EndoS either in vitro or in vivo had a reduced activity in vivo in mice. Accordingly, EndoS can be used to treat or prevent diseases or conditions mediated by IgE antibodies.

The present invention provides a method for treating or preventing diseases or conditions mediated by IgE antibodies, which method comprises administering to a subject an EndoS polypeptide or a polynucleotide encoding an EndoS polypeptide Polypeptides The EndoS polypeptide of the invention includes an EndoS polypeptide, a fragment of an EndoS polypeptide, a variant of an EndoS polypeptide, or a variant of a fragment of an EndoS polypeptide, provided that said polypeptide, fragment, variant or variant of fragment have IgE endoglycosidase activity.

Figure 2:
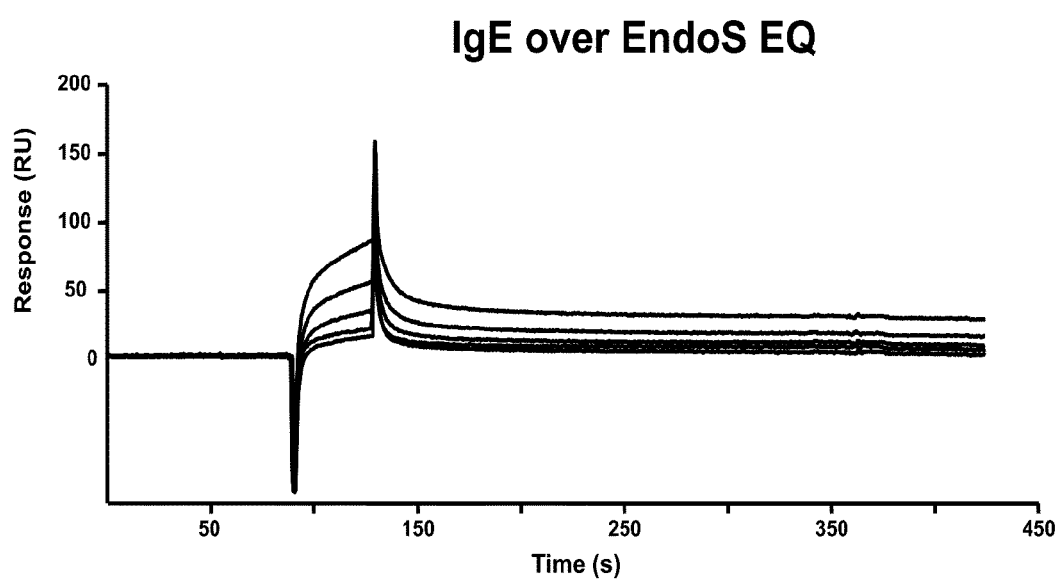
FIG. 2. EndoS interacts with IgE. Readout of surface plasmon resonance analysis for IgE passed over immobilized EndoS (E235Q).
Figure 3:
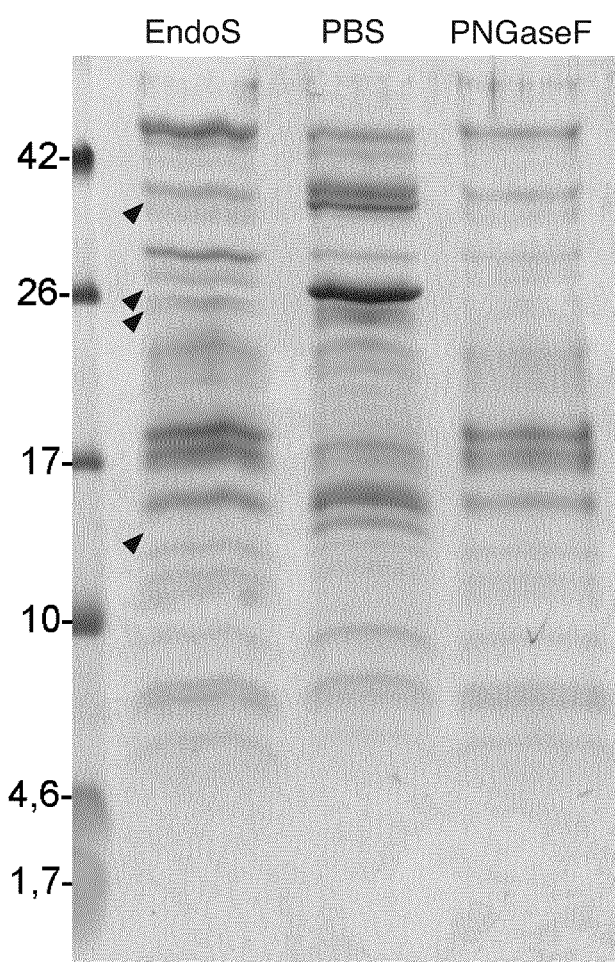
FIG. 3. EndoS unprotects IgE for proteolysis. Native IgE treated with EndoS, PBS or PNGaseF was subsequently treated with trypsin and separated on a 10% SDS-PAGE. Arrows indicate fragment appearing exclusively in EndoS treated samples.

The EndoS polypeptide is preferably *S. pyogenes* EndoS. The variant of an EndoS polypeptide may be an EndoS polypeptide from another organism, such as another bacterium. The bacterium is preferably a *Streptococcus*, such as *Streptococcus equi*, *Streptococcus zooepidemicus* or, preferably, *Streptococcus pyogenes*. Alternatively, the variant may be from *Corynebacterium pseudotuberculosis*, for example the CP40 protein; *Enterococcus faecalis*, for example the EndoE protein; or *Elizabethkingia meningoseptica* (formerly *Flavobacterium meningosepticum*), for example the EndoF$_2$ protein. The sequences of EndoS variants from various *S. pyogenes* serotypes and from *S. equi* and *S. zooepidemicus* are shown in FIG. 2. FIG. 3 shows an alignment of the α-domain of EndoS with EndoF$_2$ from *Elizabethkingia meningoseptica* and CP40 from *Corynebacterium pseudotuberculosis*.

The EndoS polypeptide may comprise or consist of:
(a) the amino acid sequence of SEQ ID NO: 1;
(b) a fragment of (a) having IgE endoglycosidase activity;
(c) a variant of (a) having at least 50% identity to the amino acid sequence of SEQ ID NO: 1 and having IgE endoglycosidase activity; or
(d) a variant of (b) having at least 50% identity to the corresponding portion of the amino acid sequence of SEQ ID NO: 1 and having IgE endoglycosidase activity.

In one embodiment, the polypeptide comprises, or consists of, the sequence of SEQ ID NO: 1. SEQ ID NO: 1 is the sequence of the mature form of EndoS, without the signal sequence, and corresponds to amino acids 37 to 995 of SEQ ID NO: 2.

The polypeptide may additionally include a signal sequence. Accordingly, the EndoS polypeptide may comprise or consist of:
(a) the amino acid sequence of SEQ ID NO: 2;
(b) a fragment of (a) having IgE endoglycosidase activity;
(c) a variant of (a) having at least 50% identity to the amino acid sequence of SEQ ID NO: 2 and having IgE endoglycosidase activity; or
(d) a variant of (b) having at least 50% identity to the corresponding part of the amino acid sequence of SEQ ID NO: 2 and having IgE endoglycosidase activity.

In one embodiment, the polypeptide comprises, or consists of, the sequence of SEQ ID NO: 2.

A fragment of the EndoS polypeptide is typically a polypeptide having IgE endoglycosidase activity, which consists of an amino acid sequence which is identical to part of the amino acid sequence of the EndoS polypeptide, but which does not consist of the entire amino acid sequence of the EndoS polypeptide. That is, a fragment of the EndoS polypeptide is typically a polypeptide having IgE endoglycosidase activity, which derives from the EndoS polypeptide but which is shorter than the EndoS polypeptide. For example, the EndoS polypeptide of SEQ ID NO: 1 is 959 amino acids in length, and so a fragment of the EndoS polypeptide of SEQ ID NO: 1 may consist of upto 958 contiguous residues of SEQ ID NO: 1, provided the fragment has IgE endoglycosidase activity. A fragment typically consists of no more than 250, 300, 350, 400, 450, 500, 550, 600, 650, 700, 750, 800, 850, 900, 950 or 955 contiguous amino acids of the EndoS polypeptide. A fragment typically consists of at least 10, 20, 30, 40, 50, 100, 200 or more contiguous amino acids of the EndoS polypeptide.

Preferably, the fragment of the EndoS polypeptide used in the invention encompasses residues 191 to 199 of SEQ ID NO: 1, i.e. Leu-191, Asp-192, Gly-193, Leu-194, Asp-195, Val-196, Asp-197, Val-198 and Glu-199 of SEQ ID NO: 1 (residues 227 to 235 of SEQ ID NO: 2, i.e. Leu-227, Asp-228, Gly-229, Leu-230, Asp-231, Val-232, Asp-233, Val-234 and Glu-235 of SEQ ID NO: 2). These amino acids constitute a perfect chitinase family 18 active site, ending with glutamic acid. The glutamic acid in the active site of chitinases is typically essential for enzymatic activity.

A preferred fragment of SEQ ID NO: 2 consists of amino acids 37 to 995 of SEQ ID NO: 2, i.e. SEQ ID NO: 1, which corresponds to the form of EndoS secreted from *S. pyogenes* after removal of the signal peptide. Another preferred fragment of the invention consists of amino acids 1 to 409 of SEQ ID NO: 1 (amino acids 37 to 445 of SEQ ID NO: 2), which corresponds to the enzymatically active α-domain of EndoS generated by cleavage by the streptococcal cysteine proteinase SpeB.

A variant of the EndoS polypeptide is typically a polypeptide which has an amino acid sequence that varies from that in SEQ ID NO: 1 or SEQ ID NO: 2, but which has IgE endoglycosidase activity. Typically, a variant of the invention has at least 50%, 55% or 65% identity, preferably at least 70%, at least 80%, at least 90% and particularly preferably at least 95%, at least 97% or at least 99% identity, with the amino acid sequence of SEQ ID NO: 1 or SEQ ID NO: 2. Such variants may include allelic variants and the deletion, modification or addition of single amino acids or groups of amino acids within the protein sequence, as long as the polypeptide has IgE endoglycosidase activity. The identity of variants of SEQ ID NO: 1 or SEQ ID NO: 2 may be measured over a region of at least 100, at least 250, at least 500, at least 750, at least 800, at least 850, at least 900, at least 950, at least 955 or more contiguous amino acids of the sequence shown in SEQ ID NO: 1 or SEQ ID NO: 2, or more preferably over the full length of SEQ ID NO: 1 or SEQ ID NO: 2.

In one embodiment, the variant of the EndoS polypeptide used in the invention comprises a sequence which consists of residues 191 to 199 of SEQ ID NO: 1. That is Leu-191, Asp-192, Gly-193, Leu-194, Asp-195, Val-196, Asp-197, Val-198 and Glu-199 of SEQ ID NO: 1 (which correspond to residues 227 to 235 of SEQ ID NO: 2, i.e. Leu-227, Asp-228, Gly-229, Leu-230, Asp-231, Val-232, Asp-233, Val-234 and Glu-235 of SEQ ID NO: 2). In one embodiment, the variant comprises a sequence which consists of residues 191 to 199 of SEQ ID NO: 1 modified by at least one deletion or substitution, preferably a conservative solution. In one such embodiment, position 199 is not modified or deleted, and thus glutamic acid is present at position 199. Therefore, a variant of SEQ ID NO: 1 preferably contains Glu-199 of SEQ ID NO: 1 and a variant of SEQ ID NO: 2 preferably contains Glu-235 of SEQ ID NO: 2.

A variant of a fragment of the EndoS polypeptide is also contemplated. In this embodiment, the variant is a polypeptide which has at least about 50%, 55% or 65% identity, preferably at least 70%, at least 80%, at least 90% and particularly preferably at least 95%, at least 97% or at least 99% identity to the part of the amino acid sequence of the EndoS polypeptide which is represented by the fragment, provided that the variant of the fragment has IgE endoglycosidase activity. This identity is preferably measured over the full length of the part of the amino acid sequence of the EndoS polypeptide which is represented by the fragment. For example, where the fragment consists of amino acids 1 to 409 of SEQ ID NO: 1, a variant of said fragment has the indicated sequence identity level over the whole 409 amino acid length of said fragment.

Typically, the fragment, the variant, or the variant of the fragment of the EndoS polypeptide has an IgE-specific activity which is at least equivalent to that of EndoS polypeptide. Preferably, the fragment, the variant, or the variant of the fragment of the EndoS polypeptide has an IgE-specific activity which is improved compared to that of EndoS polypeptide. IgE-specific activity typically refers to affinity for IgE and/or IgE endoglycosidase activity and/or the ability to remove IgE from the surface of a basophil and/or a mast cell and/or the ability to reduce IgE activity in vivo. These functional characteristics may be determined by any appropriate method. Examples of appropriate methods are described herein.

The fragment, the variant, or the variant of the fragment of the EndoS polypeptide may have reduced binding affinity for IgG and/or reduced IgG endoglycosidase activity compared to the EndoS polypeptide. The reduced IgG binding affinity and/or reduced IgG endoglycosidase activity is preferably reduced binding affinity and/or endoglycosidase activity for IgG1 and/or IgG2, and may be determined by any appropriate method.

Amino acid identity may be calculated using any suitable algorithm. For example the UWGCG Package provides the BESTFIT program which can be used to calculate homology (for example used on its default settings) (Devereux et at (1984) *Nucleic Acids Research* 12, 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et at (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made. The modified polypeptide generally retains activity as an IgE endoglycosidase. The substitutions are preferably conservative substitutions, for example according to the following Table. Amino acids in the same block in the second column and preferably in the same line in the third column may be substituted for each other:

| ALIPHATIC | Non-polar | G A P |
|           |           | I L V |
|           | Polar - uncharged | C S T M |
|           |           | N Q |
|           | Polar - charged | D E |
|           |           | K R |
| AROMATIC |           | H F W Y |

A polypeptide used in the invention may be chemically modified, e.g. post-translationally modified. For example, they may be glycosylated, phosphorylated or comprise modified amino acid residues. They may be modified by the addition of histidine residues to assist their purification or by the addition of a signal sequence to promote insertion into the cell membrane. Such modified polypeptides fall within the scope of the term "polypeptide" used herein.

Polypeptides for use in the invention may be in isolated form. It will be understood that the polypeptide may be mixed with carriers or diluents which will not interfere with the intended purpose of the polypeptide and still be regarded as isolated. Such carriers or diluents are preferably pharmaceutically acceptable.

A polypeptide for use in the invention may also be in a purified form, in which case it will generally comprise the polypeptide in a preparation in which more than 50%, e.g. more than 80%, 90%, 95% or 99%, by weight of the polypeptide in the preparation is a polypeptide of the invention.

Polypeptides for use in the present invention may be isolated from any suitable organism that expresses an EndoS polypeptide or a variant of an EndoS polypeptide. Typically, the EndoS polypeptide is isolated from suitable EndoS expressing strains of *Streptococcus*, preferably strains of *S. pyogenes*. Suitable organisms and strains may be identified by a number of techniques. For example, *S. pyogenes* strains may initially be tested for the presence an ndoS gene. Polynucleotide primers or probes may be designed based on, for example, SEQ ID NOs: 1, 2 or 3. The presence of the ndoS gene can then be verified by PCR using such primers or by hybridisation of probes to genomic DNA of the *S. pyogenes* strain.

Streptococcal strains expressing active EndoS or a variant thereof can be identified by assaying for IgE endoglycosidase activity in the culture supernatant or by immunodetection using antibodies directed towards EndoS. The Streptococcal strains that have been verified as expressing active EndoS are the *S. pyogenes* M1 serotype strains AP1 and SF370, the *S. equi* strain 4047 and the *S. zooepidermicus* strain H70. In addition, the ndoS gene is found in the following *S. pyogenes* strains: M1 serotype strains SSI-1 and MGAS5005, M2 serotype strain MGAS10270, M3 serotype strain MGAS315, M4 serotype strain MGAS10750, M5 serotype strain Manfredo, M6 serotype strain MGAS10394, M12 serotype strain MGAS9429, M18 serotype strain MGAS8232, M28 serotype strain MGAS6180 and M49 serotype strain 591.

Isolation and purification of EndoS from an expressing *S. pyogenes* culture, or from cultures of other cells expressing EndoS is typically on the basis of IgE endoglycosidase activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for IgE endoglycosidase activity and peak activity fractions may be pooled. Fractions may be analysed by SDS PAGE. Fractions may be stored at −80° C. In an alternative method to purify EndoS, EndoS without the signal sequence (i.e. having the sequence of SEQ ID NO: 1) is expressed in *Escherichia coli* using GST Gene Fusion System (Amersham-Pharmacia Biotech, Uppsala, Sweden). A 2929 base pair PCR product covering bases 304 to 3232 of the ndoS sequence is amplified from *S. pyogenes* genomic DNA using primers 5'-ACT-GGG-ATC-CCG-GAG-GAG-AAG-ACT-3' with a BamHI site (underlined) and 5'-TTA-AT C-TCG-AGG-TTG-CTA-TCT-AAG-3' with an XhoI site (underlined). This fragment is digested with BamHI and XhoI and ligated into the pGEX-5X-3 generating plasmid pGEXndoS that is used to transform *E. coli* BL21(DE3) pLys. pGEXndoS/BL21(DE3)pLys is induced with 0.1 mM isopropyl β-D-thiogalactopyranoside. After induction, bacteria are lysed using BugBuster™ (Novagen) and the GST-EndoS fusion protein is purified on Glutathione-Sepharose®. The GST tag is removed using factor Xa according to protocols (Amersham-Pharmacia Biotech), and residual factor Xa is removed using Xarrest™-agarose (Novagen). This results in a preparation of recombinant EndoS (rEndoS) that is homogenous as assessed by SDS-PAGE and Western blot using EndoS-specific antibodies. Prior to in vivo experiments protein samples are sterile-filtered through a 0.2 μm filter (Millipore). Purified EndoS protein is stored at −80° C. in phosphate buffered saline.

Polypeptides for use in the invention may also be prepared as fragments of such isolated polypeptides. Further, the EndoS polypeptides may also be made synthetically or by recombinant means. For example, a recombinant EndoS polypeptide may be produced by transfecting mammalian cells in culture with an expression vector comprising a nucleotide sequence encoding the polypeptide operably linked to suitable control sequences, culturing the cells, extracting and purifying the EndoS polypeptide produced by the cells.

The amino acid sequence of polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

Polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the EndoS polypeptides, provided that the polypeptides retain IgE endoglycosidase activity.

Polynucleotides

A polynucleotide encoding a polypeptide of the invention may be used to treat or prevent a disease or condition mediated by IgE antibodies. In particular the polynucleotide may comprise or consist of: (a) the coding sequence of SEQ ID NO: 3; (b) a sequence which is degenerate as a result of the genetic code to the sequence as defined in (a); (c) a sequence having at least 60% identity to a sequence as defined in (a) or (b) and which encodes a polypeptide having IgE endoglycosidase activity; or (d) a fragment of any one of the sequences as defined in (a), (b) or (c) which encodes a polypeptide having IgE endoglycosidase activity.

Typically the polynucleotide is DNA. However, the polynucleotide may be a RNA polynucleotide. The polynucleotide may be single or double stranded, and may include within it synthetic or modified nucleotides.

A polynucleotide of the invention can typically hybridize to the coding sequence or the complement of the coding sequence of SEQ ID NO: 3 at a level significantly above background. Background hybridization may occur, for example, because of other DNAs present in a DNA library. The signal level generated by the interaction between a polynucleotide of the invention and the coding sequence or complement of the coding sequence of SEQ ID NO: 3 is typically at least 10 fold, preferably at least 100 fold, as intense as interactions between other polynucleotides and the coding sequence of SEQ ID NO: 3. The intensity of interaction may be measured, for example, by radiolabelling the probe, e.g. with $^{32}$P. Selective hybridisation may typically be achieved using conditions of medium to high stringency. However, such hybridisation may be carried out under any suitable conditions known in the art (see Sambrook et al, Molecular Cloning: A Laboratory Manual, 1989). For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 3 may be modified by nucleotide substitutions, for example from 1, 2 or 3 to 10, 25, 50, 100, 200, 500 or 750 substitutions. The polynucleotide of SEQ ID NO: 3 may alternatively or additionally be modified by one or more insertions and/or deletions and/or by an extension at either or both ends. Additional sequences such as signal sequences may also be included. The modified polynucleotide generally encodes a polypeptide which has IgE specific endoglycosidase activity. Degenerate substitutions may be made and/or substitutions may be made which would result in an amino acid substitution when the modified sequence is translated. The substitution may be conservative, for example as shown in the Table above.

A nucleotide sequence which is capable of selectively hybridizing to the complement of the DNA coding sequence of SEQ ID NO: 3 will generally have at least 60%, at least 70%, at least 80%, at least 90%, at least 95%, at least 98% or at least 99% sequence identity to the coding sequence of SEQ ID NO: 3 over a region of at least 20, preferably at least 30, for instance at least 40, at least 60, at least 100, at least 200, at least 500, more preferably at least 750 contiguous nucleotides or most preferably over the full length of SEQ ID NO: 3 or the length of SEQ ID NO: 3 encoding a polypeptide having the sequence shown in SEQ ID NO: 1 or 2. Sequence identity may be determined by any suitable method, for example as described above.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 60, preferably over 100 nucleotides forms one aspect of the invention, as does a polynucleotide which has at least 95% sequence identity over 500 nucleotides.

Polynucleotide fragments will preferably be at least 20, for example at least 25, at least 30 or at least 50 nucleotides in length. They will typically be up to 100, 150, 250 or 500 nucleotides in length. Fragments can be longer than 500 nucleotides in length, for example up to 600, 700, 800, 900, 1000, 1500, 2000, 2500 or 3000 nucleotides in length, or even up to a few nucleotides, such as five, ten or fifteen nucleotides, short of the coding sequence of SEQ ID NO: 3.

Polynucleotides for use in the invention may be produced recombinantly, synthetically, or by any means available to those of skill in the art. They may also be cloned by standard techniques. The polynucleotides are typically provided in isolated and/or purified form.

In general, short polynucleotides will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the ndoS gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the ndoS gene sequence described herein. Although in general the techniques mentioned herein are well known in the art, reference may be made in particular to Sambrook et al. (1989).

EndoS polynucleotides as described herein have utility in production of the polypeptides for use in the present invention, which may take place in vitro, in vivo or ex vivo. The polynucleotides may be used as therapeutic agents in their own right or may be involved in recombinant protein synthesis.

The polynucleotides for use in the invention are typically incorporated into a recombinant replicable vector. The vector may be used to replicate the nucleic acid in a compatible host cell. Therefore, polynucleotides for use in the invention may be made by introducing an EndoS polynucleotide into a replicable vector, introducing the vector into a compatible host cell and growing the host cell under conditions which bring about replication of the vector. The host cell may, for example, be an E. coli cell.

Preferably the vector is an expression vector comprising a nucleic acid sequence that encodes an EndoS polypeptide. Such expression vectors are routinely constructed in the art of molecular biology and may for example involve the use of plasmid DNA and appropriate initiators, promoters, enhancers and other elements, such as for example polyadenylation signals, which may be necessary and which are positioned in the correct orientation in order to allow for protein expression. Other suitable vectors would be apparent to persons skilled in the art. By way of further example in this regard we refer to Sambrook et al. (1989).

Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vector is typically adapted to be used in vivo.

Promoters and other expression regulation signals may be selected to be compatible with the host cell for which expression is designed. Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences. This will allow the introduction of the polynucleotides of the invention into the genome of eukaryotic cells by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Functional Characteristics of Polypeptides

Typically, a polypeptide of the invention displays immunoglobulin endoglycosidase activity, and in particular IgE endoglycosidase activity. Preferably, the polypeptide hydrolyzes an asparagine-linked glycan in the Cε3 domain of IgE. The glycan may be linked to Asn-371, Asn-394 or Asn-383. The polypeptide may hydrolyze one, two or all three of these glycans. The polypeptide may typically hydrolyze the β-1, 4-di-N-acetylchitobiose core of the asparagine-linked glycan.

Endoglycosidase activity may be determined by means of a suitable assay. For example, a test polypeptide may be incubated with IgE at a suitable temperature, such as 37° C., and subsequently incubated with an immunoglobulin specific protease such as trypsin. The starting materials and the reaction products may then be analysed by SDS PAGE. Typically, more bands corresponding to molecules with reduced molecular mass are observed if the test polypeptide has IgE endoglycosidase activity, as compared to the bands observed when a irrelevant/inactive control substance, e.g. PBS, is incubated with IgE prior to protease treatment.

Another assay for determining whether a test polypeptide has IgE endoglycosidase activity is by detection of glycosylated IgE using *Lens culinaris* agglutinin lectin (LCA), optionally using horseradish peroxidase and peroxidase substrate. Typically, the carbohydrate signal is reduced if the test polypeptide has IgE endoglycosidase activity. Another assay for determining whether a test polypeptide has IgE endoglycosidase activity is by incubation of a test polypeptide with purified IgE Fc fragments followed by reduction of the sample with 10 mM dithiotreitol and mass spectroscopy (MALDI-TOF) analysis. Typically, the mass of monomeric IgE Fc is reduced if the test polypeptide has IgE endoglycosidase activity. The reduction in mass is typically about 3,000 to about 6,000 Da. The endoglycosidase activity of the polypeptides can be further characterised by inhibition studies. The polypeptide preferably has IgE endoglycosidase activity which is greater than or equal to the IgE endoglycosidase activity of a polypeptide consisting of the amino acid sequence of SEQ ID NO: 1. That is, the polypeptide preferably has equal or greater IgE endoglycosidase activity when compared to the IgE endoglycosidase activity of a polypeptide consisting of the amino acid sequence of SEQ ID NO: 1.

The polypeptide is capable of hydrolyzing IgE molecules present in the subject to be treated. Thus, where the subject is a human, the polypeptide is capable of hydrolyzing human IgE. In preferred embodiments, the polypeptide has the ability to hydrolyze human, Rhesus monkey, mouse, rat, rabbit, horse, goat, dog and swine IgE.

Typically, a polypeptide of the invention is capable of binding to IgE. In preferred embodiments, the polypeptide has the ability to bind to human, Rhesus monkey, mouse, rat, rabbit, horse, goat, dog and swine IgE.

The binding affinity of a polypeptide of the invention for IgE may be assessed by any suitable method. One approach involves generating an enzymatically inactive form of the polypeptide to act as an analogue for the polypeptide in binding affinity assessments. The resulting determination of affinity for the enzymatically inactive form indicates the affinity of the active form of the polypeptide. For example, the interaction between immobilised IgE and an enzymatically inactive form of the polypeptide can be assessed using Surface Plasmon Resonance spectroscopy, competition binding assays, or direct binding assays using a labeled form of the enzymatically inactive form of the polypeptide. This will determine the binding affinity of the inactive form polypeptide for IgE, which is also the binding affinity of the active polypeptide for IgE. The affinity of the active polypeptide may also be determined directly by these methods.

An enzymatically inactive form of the polypeptide may typically be generated by modification of the chitinase family 18 active site, for example by removing or substituting the glutamic acid at the C terminal end of said site. Thus, for example, a polypeptide of SEQ ID NO: 1 containing Glutamine in place of Glutamic acid at position 199 of SEQ ID NO: 1 (position 235 of SEQ ID NO: 2) is enzymatically inactive. This particular inactive EndoS polypeptide may be referred to as E235Q.

Affinity may typically be expressed in terms of the equilibrium dissociation constant ($K_D$) for a given binding interaction. The polypeptide preferably has an affinity for IgE which is greater than or equal to the affinity for IgE of a polypeptide consisting of the amino acid sequence of SEQ ID NO: 1. That is, the polypeptide preferably has equal or greater affinity (equal or lower $K_D$) for IgE when compared to the affinity for IgE of a polypeptide consisting of the amino acid sequence of SEQ ID NO: 1. The binding interaction between the polypeptide of the invention and IgE preferably has a $K_D$ less than or equal to about 133 nM.

Typically, a polypeptide of the invention is able to remove IgE bound to the surface of a basophil or a mast cell in human blood. The polypeptide may remove IgE from more than 50% of the basophils and/or mast cells in a sample of human blood, preferably more than 55%, 60%, 65%, 70%, 75%, 80%, 90% or 95% of the basophils and/or the mast cells in a sample of human blood. The polypeptide may remove IgE from 100% of the basophils and/or the mast cells in a sample of human blood.

Removal of IgE bound to the surface of basophils or mast cells may be assessed by any suitable method. One method involves analysis of the basophil or mast cell surface for the presence or absence of IgE using a labelled anti-IgE antibody. The cell surface may typically be analysed using a fluorescently labelled antibody and fluorescence-activated cell sorting.

The polypeptide preferably has an ability to remove IgE from the surface of a basophil and/or a mast cell which is greater than or equal to the ability of a polypeptide consisting of the amino acid sequence of SEQ ID NO: 1 to remove IgE from the surface of the corresponding cell type. That is, the polypeptide preferably has equal or greater ability to remove IgE from the surface of a basophil and/or a mast cell when compared to the ability of a polypeptide consisting of the amino acid sequence of SEQ ID NO: 1 to remove IgE from the surface of the corresponding cell type. That is, preferably, the polypeptide has equal or greater ability to remove IgE from the surface of a basophil when compared to the ability of a polypeptide consisting of the amino acid sequence of SEQ ID NO: 1 to remove IgE from the surface of a basophil, and/or the polypeptide has equal or greater ability to remove IgE from the surface of a mast cell when compared to the ability of a polypeptide consisting of the amino acid sequence of SEQ ID NO: 1 to remove IgE from the surface of a mast cell.

Typically, a polypeptide of the invention is able to reduce the activity of IgE in vivo. For example, the polypeptide may typically be able to reduce or eliminate a symptom or symptoms associated with a disease or condition mediated by IgE antibodies. The ability of a polypeptide of the invention to reduce the activity of IgE in vivo may be assessed by any suitable method.

One method involves the use of a model disorder mediated by IgE antibodies. Such models are known in the art and may be referred to as Passive Cutaneous Anaphylaxis (PCA) models. An example involves the induction of atopic/allergic responses to a model allergen such as 2,4-Dinitrophenol (DNP). Typically, the first step is passive sensitisation of a mouse with anti-DNP IgE injected intradermally into one or both ears. The mouse is then challenged approximately 1 day later with an intravenous injection of human serum albumin coupled to DNP (HSA DNP) in PBS containing a dye such as Evans blue. Approximately 1 hour later the ears are examined for the presence of a symptom or symptoms of an atopic or allergic reaction, typically edema/swelling in the skin of the ear. This will be indicated by the visible presence of dye beneath the skin. The larger the dyed area, the greater the reaction/more severe the symptom.

To determine whether a polypeptide of the invention is able to reduce the activity of IgE in this model, a mouse may be injected with the intraperitoneally approximately 6 to 10 hours after the injection of anti-DNP IgE, with a control mouse receiving an intraperitoneal injection of an inactive substance such as PBS. A smaller dyed area of ear in the mouse receiving the polypeptide compared to the control mouse indicates that the polypeptide has reduced the activity of IgE in vivo.

The polypeptide preferably has an ability to reduce the activity of IgE in vivo which is greater than or equal to the ability to reduce the activity of IgE in vivo of a polypeptide consisting of the amino acid sequence of SEQ ID NO: 1. That is, the polypeptide preferably has equal or greater ability to reduce the activity of IgE in vivo when compared to the ability to reduce the activity of IgE in vivo of a polypeptide consisting of the amino acid sequence of SEQ ID NO: 1.

Diseases and Conditions

The EndoS polypeptide, or polynucleotide, may be used to treat or prevent diseases or conditions mediated by IgE antibodies. The IgE antibodies which mediate a disease or condition may be described as pathogenic. It is well known in the art that IgE antibodies are involved in the pathogenesis of a number of different diseases and conditions. The present inventors have found that the role of pathogenic IgE antibodies in such diseases can be inhibited using an EndoS polypeptide or polynucleotide.

The disease or condition is typically characterised by the presence of at least one of the following symptoms:

| Affected organ | Symptom |
| --- | --- |
| Nose | Swelling of the nasal mucosa (allergic rhinitis) |
| Sinuses | Allergic sinusitis |
| Eyes | Redness and itching of the conjunctiva (allergic conjunctivitis) |
| Airways | Sneezing, coughing, bronchoconstriction, wheezing and dyspnea, sometimes outright attacks of asthma (atopic/allergic asthma), in severe cases the airway constricts due to swelling known as laryngeal edema |
| Ears | Feeling of fullness, possibly pain, and impaired hearing due to the lack of eustachian tube drainage |
| Skin | Rashes, swelling and inflammation (often localised to point of contact with allergen), e.g. eczema (atopic dermatitis), hives (urticaria), angioedema |
| Gastrointestinal tract | Abdominal pain, bloating, vomiting, diarrhoea |
| Other | Hypotension, anaphylaxis |

The disease or condition is typically a disorder in which undesirable IgE production and/or excessive, harmful or unwanted activation of basophils and/or mast cells occurs.

Undesirable IgE prediction typically means the presence of high levels of total IgE in the serum of an individual in the absence of infection by a parasite. A high level of total serum IgE is typically greater than about 80 IU/ml.

Excessive, harmful or unwanted basophil and/or mast cell activation typically means activation of basophils and/or mast cells in the absence of infection by a parasite. Activation of basophils and/or mast cells may be defined as degranulation to release histamine and/or other substance including proteoglycans (e.g. heparin and chondroitin), and proteolytic enzymes (e.g. elastase and lysophospholipase). Activated basophils also secrete leukotrienes, and several cytokines, in particular IL-4.

Whether or not a basophil has been activated can be determined by any suitable method. One method involves analysis of the basophil surface for the presence or absence of CD203 using a labelled anti-CD203 antibody, wherein the presence of CD203 indicates that a basophil is activated. The cell surface may typically be analysed using a fluorescently labelled antibody and fluorescence-activated cell sorting.

Whether or not a mast cell has been activated can be determined by any suitable method. One method includes analysis of the mast cell by histology staining. Activation is indicated by a the lack of uniform staining, and/or reduction in staining by >30% and the presence of extracellular tryptase. Mast cell activation may be confirmed by staining a sample metachromatically with acidified (pH 2) 0.1% Toluidine blue (TB) for 5 min at room temperature. TB binds to heparin in secretory granules and changes its color to red-purple on binding (metachromasia).

The disease or condition may be an atopic disorder, an allergic or hypersensitivity reaction, or hyper-IgE syndrome. The atopic disorder or allergic or hypersensitivity reaction is typically characterised by an immune response to an allergen. The immune response is typically characterised by the production of IgE specific for the allergen. Allergens include pollens, animal dander (in particular cat dander), grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; epidermal allergens can be obtained from house or organic dusts (typically fungal in origin), from arthropods such as house mites (*Dermatophagoides pteronyssinus*), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. The allergen may be a therapeutic agent, particularly an anti-cancer agent. The anti-cancer agent may be a chemotherapeutic agent or a therapeutic antibody. Examples of suitable chemotherapeutic agents include carboplatin, cisplatin, oxaliplatin, paclitaxel (taxol), docetaxel (taxotere), peplomycin, and doxorubicin. Examples of suitable therapeutic antibodies include rituximab, infliximab, omalizumab, basiliximab, trastuzumab, abciximab, natalizumab, and cetuximab.

Particularly well characterized allergens include, but are not limited to, the major allergen produced by the domestic cat Felis catus (Felis domesticus) glycoprotein Fel d1, the major and cryptic epitopes of the Der p I allergen (Hoyne et al. (1994) Immunology 83190-195), bee venom phospholipase A2 (PLA) (Akdis et al. (1996) J. Clin. Invest. 98:1676-1683), birch pollen allergen Bet v 1 (Bauer et al. (1997) Clin. Exp. Immunol. 107:536-541), and the multi-epitopic recombinant grass allergen rKBG8.3 (Cao et al. (1997) Immunology 90:46-51).

The allergen may be selected from: a plant allergen (particularly a grass allergen), animal dander allergens, a mold or fungal allergen, a dust allergen, a dust mite allergen, a stinging insect venom, an environmental allergen, a food allergen or a therapeutic agent.

The allergen may be cat dander protein Fel d1; House dust mite proteins Der P1, Der P2 and Der P7; Ragweed protein amb a 1.1, a 1.2, a1.3 or a1.4; Rye grass proteins lo1 p1 and lo1 p5; Timothy grass proteins phl p1 and phl p5; Bermuda grass protein Cyn d 5; Alternaria alternate proteins Alt a 1, Alt a 2 and Enolase (Alt a 6); Birch protein Bet v1 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut protein Ara h1, Ara h2, Ara h3, Ara h4, Ara h5, Ara h6, a plant profilin, a lipid transfer protein, or an anti-cancer agent.

The subject to be treated is typically a mammalian subject, such as a mouse, rat or primate (e.g. a marmoset or monkey). The subject may be human or a non-human animal. Where the subject is a laboratory animal such as a mouse, rat or primate, the animal may be treated to induce a disease or condition mediated by pathogenic IgE antibodies. For example, a passive cutaneous anaphylaxis (PCA) model may be used.

Therapy and Prophylaxis

The present invention provides the use of polypeptides and polynucleotides of the invention to treat or prevent a disease or condition mediated by pathogenic IgE antibodies.

In a specific embodiment, the present invention provides the use of polypeptides and polynucleotides of the invention to treat or prevent a hypersensitivity reaction to a therapeutic agent in an individual. The therapeutic agent is typically an anti-cancer agent.

Treatment may be therapeutic or prophylactic. The polypeptide or polynucleotide may be administered to an individual in order to prevent the onset of one or more symptoms of the disease or condition. In this embodiment, the subject may be asymptomatic. The subject may have a genetic predisposition to the disease. A prophylactically effective amount of the polypeptide or polynucleotide is administered to such an individual. A prophylactically effective amount is an amount which prevents the onset of one or more symptoms of a disease or condition.

A therapeutically effective amount of the polypeptide or polynucleotide is an amount effective to ameliorate one or more symptoms of a disease or condition. Preferably, the individual to be treated is human.

The polypeptide or polynucleotide may be administered to the subject by any suitable means or route. The polypeptide or polynucleotide may be administered by an enteral or parenteral route. The polypeptide or polynucleotide may be administered orally (e.g. as tablets, troches, lozenges, aqueous or oily suspensions, dispersible powders or granules), topically, parenterally, intraperitoneally, subcutaneously, by inhalation, intravenously, intramuscularly, intrasternally, transdermally, intradermally, sublingually, anally, intranasally, buccally, by pulmonary, intra-arterial, intraarticular, or intraocular routes, or by infusion techniques, or by any other appropriate route.

The polypeptide or polynucleotide may be administered to the subject in such a way as to target therapy to a particular site. For example, a polypeptide may be administered directly to the site of an allergic or atopic reaction, for example the site of a rash and/or edema. The polypeptide may be applied topically to such a site. The polypeptide may be injected locally, for example subcutaneously or intradermally, at such a site. For polynucleotides, expression vectors encoding the polypeptide may be used to direct expression of the polypeptide to a particular tissue, for example by using tissue-specific promoters or RNAi.

The formulation of any of the polypeptides and polynucleotides mentioned herein will depend upon factors such as the nature of the polypeptide or polynucleotide and the condition to be treated. The polypeptide or polynucleotide may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The polypeptide or polynucleotide may also be administered as suppositories. A physician will be able to determine the required route of administration for each particular patient.

Typically the polypeptide or polynucleotide is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically effective amount of polypeptide or polynucleotide is administered. The dose may be determined according to various parameters, especially according to the polypeptide or polynucleotide used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The polynucleotide sequences described above and expression vectors containing such sequences can also be used as pharmaceutical formulations as outlined above. Preferably, the nucleic acid, such as RNA or DNA, in particular DNA, is provided in the form of an expression vector, which may be expressed in the cells of the individual to be treated. The vaccines may comprise naked nucleotide sequences or be in combination with cationic lipids, polymers or targeting systems. The vaccines may be delivered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

The present invention also provides a method of treating, ex vivo, blood taken from a patient suffering from a disease or condition mediated by pathogenic IgE antibodies comprising contacting the blood with a polypeptide of the invention. The polypeptide may thus be used for extracorporeal treatment of blood. The polypeptide may be used to treat one or more components of blood, such as plasma or serum. The ex vivo method described herein may be practised on blood that has already been removed from the body of a patient. The blood or blood product may optionally be returned to the patient after being contacted with a polypeptide of the invention.

Other Embodiments

The polypeptide of the invention may be used for the removal of glycans from IgE. Thus, the invention provides a method for removing at least one glycan from an IgE molecule, said method comprising contacting an IgE-containing sample with a polypeptide of the invention. Optionally, the method comprises the further steps of isolating and/or characterising the glycosylation state of the IgE molecules produced by the method.

In such a method, the polypeptide may be contacted with the sample containing IgE under conditions which permit IgE endoglycosidase activity to occur. Said activity can be verified using the methods described above. Isolation of IgE molecules may be carried out using any appropriate method. Human IgE can for instance be purified from human serum or culture medium from IgE producing myelomas using immunoaffinity chromatography on monoclonal anti-IgE antibodies coupled to a protein A-coated agarose matrix, or monoclonal antibodies covalently coupled to an agarose matrix. This may or may not be preceeded by an ion-exchange chromatography step. Assessment of glycosylation state may also be carried out using any appropriate method. Examples of suitable methods are described above.

The method of the invention can be used in particular to generate IgE antibodies which lack at least one glycan present on native, untreated IgE. That is, the method generates IgE antibodies which have at least one fewer glycan than native, untreated IgE antibodies. Preferably, the IgE antibodies of the method have at least one fewer glycan on the Cε3 domain of IgE. The method is typically carried out ex vivo on an IgE-containing sample. The sample may comprise one or more components of blood, such as plasma or serum.

The following Examples illustrate the invention:

Example 1

Direct Interaction Between EndoS and IgE

The interaction between an enzymatically inactive form of EndoS, EndoS (E235Q) and human IgG has been established using several methods including surface plasmon resonance spectroscopy. In order to determine if there was a physical interaction between human IgE and EndoS (E235Q), the inventors analyzed the interaction between immobilized EndoS (E235Q) and human IgE in the soluble phase using the same technique.

Purified recombinant GST-EndoS (E235Q) was diluted with 10 mM sodium acetate pH 4 and immobilized via amine coupling to different flow cells of CM5 sensorchips (BIAcore, Uppsala, Sweden). Immobilization levels were optimized to around 8000-10000 response units. Human myeloma IgE was injected in different concentrations (typically 10-1.25 υg/ml) at 35 υl/min and 25° C. over the coated surface (flow cell) (in running buffer: 10 mM Hepes, pH 7.5, 150 mM NaCl, 0.005% surfactant P20, and 3.4 mM EDTA). Between experiments, the surfaces were strictly regenerated with pulses of running buffer containing 2 M NaCl followed by an extensive wash procedure after reaching baseline. For affinity measurements, the binding and dissociation phases were monitored in a BIAcore 2000 instrument. After X and Y normalization of data, the blank curves from control flow cells of each injected concentration were subtracted. Where applicable, the association ($k_a$) and dissociation ($k_d$) rate constants were determined simultaneously using the equation for 1:1 Langmuir binding in the BIA Evaluation 4.1 software (BIAcore). The binding curves were fitted locally and the equilibrium dissociation constants ($K_D$) were calculated from mean values of the obtained rate constants.

This revealed a dose-dependent interaction between EndoS (E235Q) and IgE with an affinity ($K_D$) of 133 nM (FIG. 2). That is, EndoS binds to IgE. Accordingly, an enzymatically active form of EndoS was expected to be able to achieve enzymatic glycan hydrolysis of IgE.

Example 2

EndoS Hydrolyses IgE Glycans

The inventors hypothesized that the extensive glycosylation of IgE may protect it from the action of proteases such as trypsin. Glycans often protect the protein backbone of glycoproteins from proteolysis. Thus, if EndoS cleaves IgE glycans, EndoS-treated IgE should be more susceptible to proteolysis. To test this, 20 μg human myeloma IgE (lacking the glycan attached to Asn-383) (Merck Chemicals Ltd, Nottingham, UK) were incubated with EndoS, PNGaseF (Merck Chemicals) or PBS for 2 h at 37° C.°. After adding Glyco Protein Denaturing Buffer (Merck Chemicals) to all samples, they were incubated for 15 min at 99° C. and then cooled down to 37° C. 0.8 μg of restriction grade trypsin (Merck Chemicals Ltd) were added and the samples were incubated at 37° C. for 60 min. The samples were again denatured with reducing sample buffer and were separated on 10% SDS-PAGE followed by staining with Commassie Brilliant Blue (Sigma, St. Louis, Mo.).

PNGaseF-treated IgE provided a positive control since this enzyme is an amidase know to hydrolyze most N-linked glycans completely, leaving no carbohydrates on the protein backbone. PBS-treated IgE provided a negative control since no glycan cleavage of IgE will occur as a result of this treatment.

After trypsination samples were separated on SDS-PAGE and stained (FIG. 3). This revealed that in the EndoS-treated IgE sample several new bands appeared, and some were missing, as compared with IgE only treated with PBS prior to trypsination (FIG. 3, EndoS and PBS). In the PNGaseF-treated IgE sample many of the larger protein fragments that could be seen in the buffer treated IgE sample were missing (FIG. 3, PBS and PNGaseF). This indicates that IgE glycans do protect the protein from proteolysis. More importantly, it indicates that EndoS has the ability to hydrolyze one or more N-linked glycans in human IgE, since IgE is made susceptible to proteolysis by EndoS treatment. Similar effects were observed using thermolysin in place of trypsin (data not shown).

Example 3

EndoS Hydrolyses IgE Glycans in the Cε3 Domain

Based on the inventors' previous finding that EndoS treated IgG does not interact with the lectin *Lens culinaris* agglutinin (LCA), and that intact IgG binds strongly to LCA, the inventors used an LCA affinity matrix in order to verify and map the EndoS activity on IgE glycans.

Human IgE was treated with EndoS or PBS and trypsinated as described above. After incubation with trypsin and denaturing, samples were separated using an *Lens Culinaris* Agglutinin (LCA)-agarose. Samples were added to 20 μl LCA-agarose (Vector Laboratories, Peterborough, UK) and incubated for 10 min at RT. Samples were centrifuged at 3000 rpm for 5 min. The supernatants were collected and samples were washed with PBS and subsequently centrifuged. For elution, α-methyl mannoside and α-methyl glucoside (Vector laboratories) were added at a ratio of 1:1. Samples were incubated at RT for 10 min and subsequently centrifuged and the supernatant were collected. Both filtrate and eluate were collected and analyzed on 10% SDS-PAGE and bands of interest were excised and analyzed by MALDI-MS sequencing.

Figure 4:
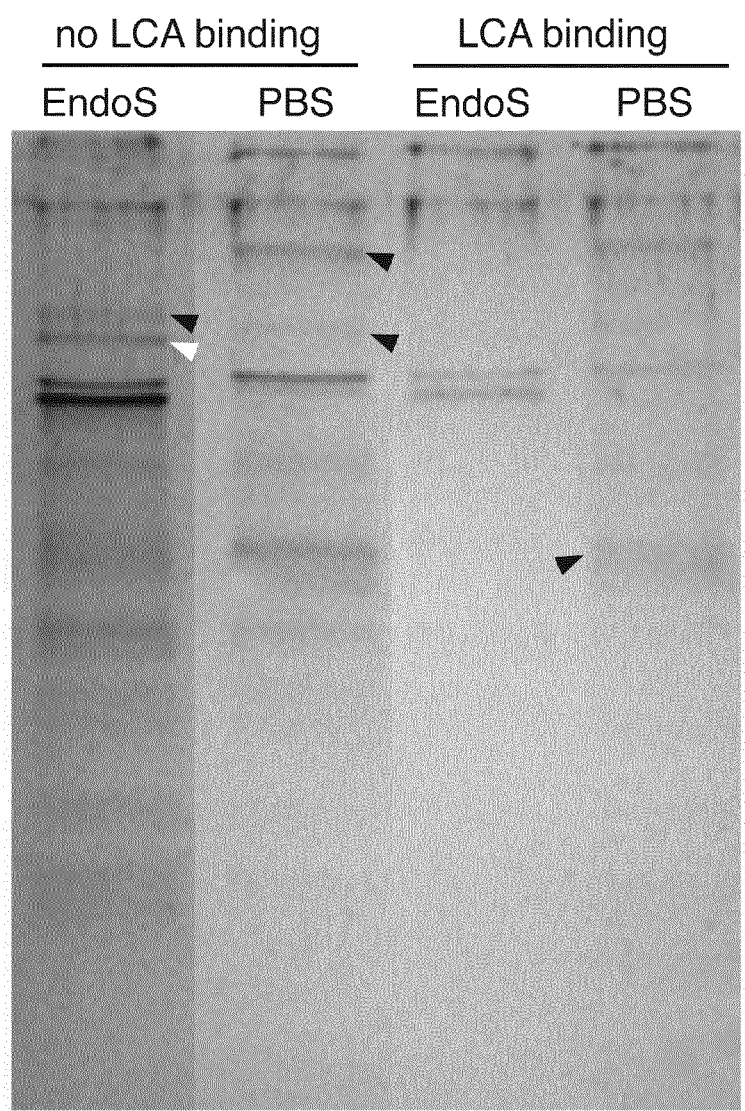
FIG. 4. Lectin affinity chromatography reveals EndoS hydrolysis of IgE glycans in the Cε3 domain. IgE was trypsinated after EndoS or PBS treatment and fragments were separated on LCA-agarose. No LCA-binding fragment contains fragments without N-linked glycans or the GlcNAc residue. LCA-binding fragments contain N-linked glycans with an intact stalk. The black arrowheads indicate samples that were analyzed with MALDI-MS. The white arrowhead indicates the only fragment from which sequence with good quality was obtained.

Filtrate (no LCA binding) and eluate (LCA binding) were separated by SDS-PAGE (FIG. 4). This revealed that in the filtrate at least two protein fragments present in the EndoS-treated sample could not be observed in the PBS-treated sample (FIG. 3, no LCA binding, EndoS and PBS), and in the eluted samples, one protein fragment could be observed in the PBS-treated while no corresponding fragment could be seen in the EndoS-treated sample (FIG. 4, LCA binding, EndoS and PBS).

EndoS or PBS unique protein fragments (black arrows) were excised from the gel and analyzed by MALDI-MS (FIG. 4, black arrows). The only peptide that could be partly sequenced (FIG. 4, white arrow) contained the two amino acid sequences YLSRPSPFDLFIR and RAAPEVYAFAT-PEWP. Sequence alignment show that these fragments originate from the Cε3 domain, which is glycosylated on Asn-371 and Asn-394 (the human myeloma IgE used is not glycosylated on Asn-383) (FIG. 1). These results indicate that EndoS hydrolyzes one or both of the glycans at Asn-371 and Asn-394 in the heavy chain Cε3 domain of human IgE.

Example 4

EndoS Inhibits Anti-IgE Mediated Basophil Activation in Whole Human Blood

In order to study if there were any functional consequences of EndoS hydrolysis of IgE glycans, the inventors investigated if EndoS could block anti-IgE mediated activation of human basophils in a whole blood environment.

Heparinized whole blood was collected from healthy volunteers. 200 μl of whole blood was incubated end over end in 37° C. for 30 min together with 20 μg GST-EndoS. Samples were split and incubated with either anti-IgE (chicken—IgY lacks N-linked glycans and it is therefore not an EndoS substrate) (Abcam, Cambridge, USA) or PBS for 15 min, 37° C. Samples were centrifuged at 300×g for 10 min followed by removal of supernatants. PBS containing 2 mM EDTA was added before repeated centrifugation. Conjugated Ab were added and incubated 15 min on ice, 500 μl cold PBS 1:20 were added, direct followed by 45 μl 10×PBS. Centrifugation was performed at 300×g for 10 min at 4° C. followed by washing two times with ice-cold PBS. Samples were subsequently analyzed by FACS on a FACSCalibur using CellQuest Pro analysis software (BD Biosciences, Franklin Lakes, N.J.).

Figure 5:
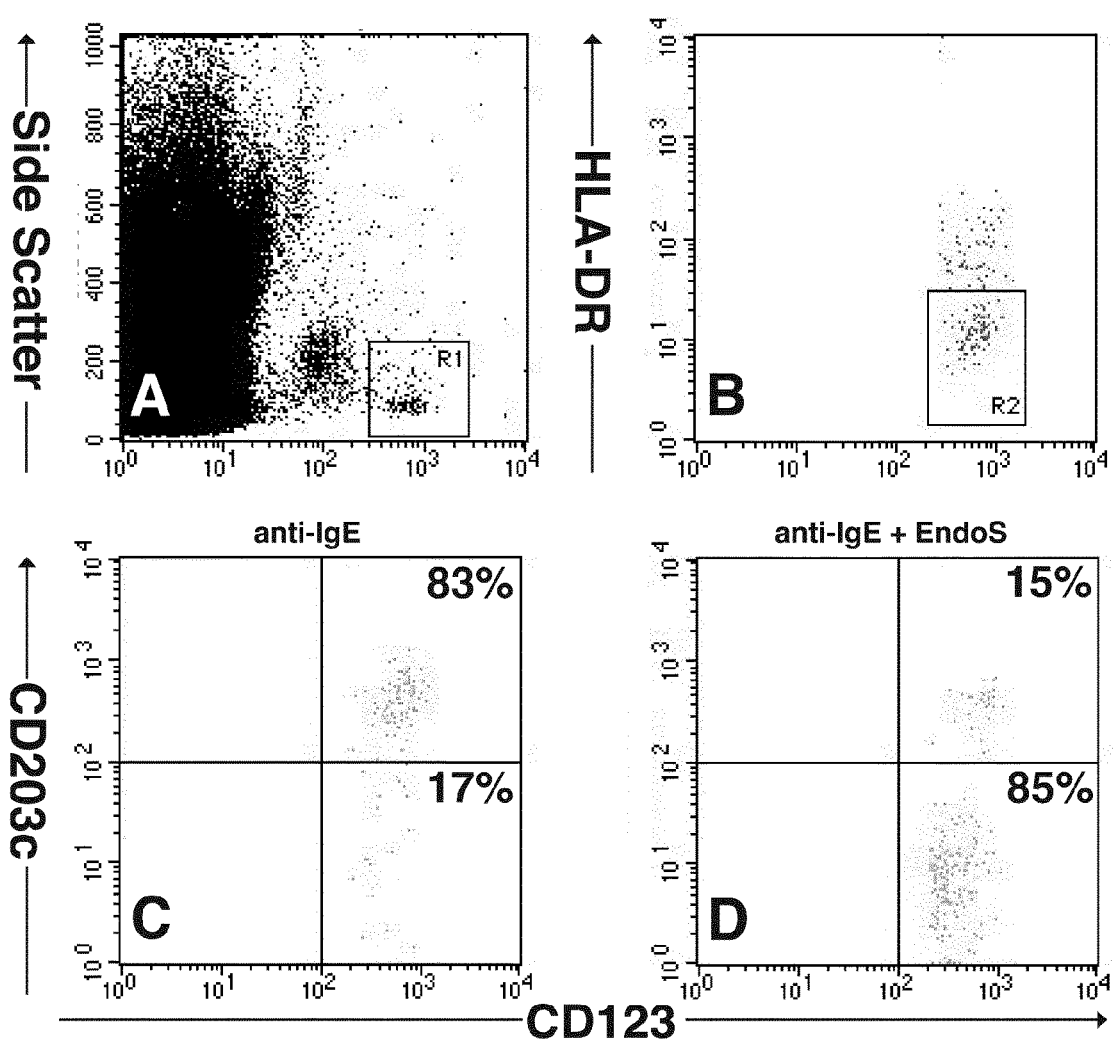
FIG. 5. EndoS inhibits anti-IgE mediated basophil activation. Whole human blood was incubated with either EndoS or PBS and later exposed to anti-IgE (chicken). Gate R1 in 5A contains 500 basophils and dendritic cells (DC) which are positive for CD123 and low SSC. DC were eliminated using HLA-DR (5B) and basophils were later characterized as activated due to the expression of CD203 on the cell surface. Without EndoS treatment 83% of the total basophil population were activated, and upon pretreatment with EndoS this population decreased to 15%.

The conjugated antibodies towards human cell markers used in all experiments were mouse anti-CD123-FITC, mouse anti-CD203c-APC (both from Miltenyi Biotech, Bergisch Gladbach, Germany), and mouse anti-HLA-DR-PerCP (Invitrogen, Carlsbad, Calif.). A first gating step identified a basophil/DC population based on side scatter (SSC) and CD123, >500 cells were counted (FIG. 5A). In a second gating step HLA-DR+ cells were excluded to obtain a pure basophil population (FIG. 5B). The basophil activity was subsequently evaluated with respect to CD203c expression on the cells within the second (R2) gate. This revealed that there is a high number (83%) of CD203c+ cells among CD123+, HLA-DR− cells in untreated samples (FIG. 5C). In contrast when blood had been treated with EndoS, there was a significant decrease in the CD203+ population, with only 15% of positive cells in the R2 gate (FIG. 5D). These results clearly indicate that EndoS inhibits anti-IgE mediated activation of human basophils in human blood.

Example 5

EndoS Removes IgE from Basophils in Whole Human Blood

Figure 6:
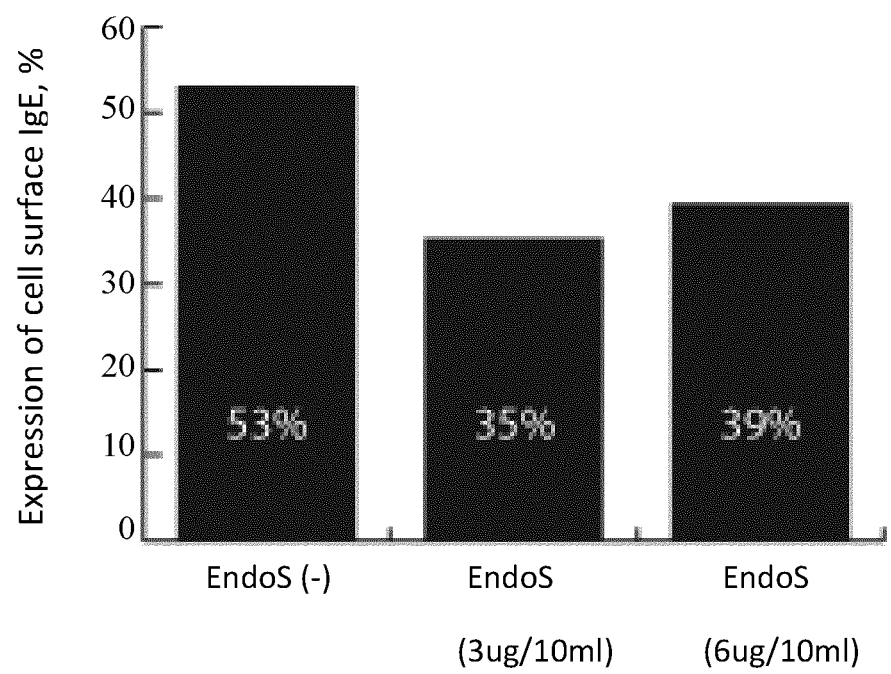
FIG. 6. EndoS removes IgE from the basophil surface. Whole blood was treated with EndoS for 2 h. Basophils and DC were later analyzed by FACS based on expression of CD123. In a second step, the percentage of cell-surface IgE was determined with labeled antibodies against IgE. The cell-surface IgE population was 53% of the total population of basophils and DC in EndoS untreated samples. Exposed to EndoS (3 ug/ml) this population decreased to 35% and to 39% with a higher dose of EndoS (6 ug/ml).

The inventors hypothesized that EndoS inhibition of basophils in part is due to hydrolysis of receptor bound IgE that would thereafter dissociate from the cells. In order to investigate this, whole blood was treated with EndoS or buffer and analyzed using FACS for surface bound IgE using mouse anti-IgE-APC (Miltenyi Biotech). Cells were gated using antibodies against CD123 as described above. This revealed that 53% of basophils from buffer treated blood gave a positive signal for surface IgE (FIG. 6, EndoS(−)). In contrast, in blood that had been treated with 0.3 or 0.6 µg/ml EndoS, only 35% and 39% of basophils were positive for IgE (FIG. 6, EndoS). These results suggest that the reduction in activation of basophils in whole blood at least in part is due to EndoS removal of IgE from the basophils surface.

Example 6

IgE Treated In Vitro with Endos has Reduced Activity In Vivo

To investigate whether EndoS treatment can interfere with IgE dependent activation of mast cells reverse passive cutaneous anaphylaxis experiments were performed.

Dinitrophenyl (DNP)-specific IgE was pretreated with either EndoS of PNGaseF. 150 µg of mouse IgE anti-DNP was treated with 10 µg EndoS or 10 U PNGaseF.

20 ng of untreated IgE, PNGaseF-treated IgE or EndoS-treated IgE was then injected intradermally into one ear and PBS as a control into the other ear of C57BL/6 mice. Common FcR gamma-chain knockout mice were used as a control, and received untreated IgE injected into one ear and PBS into the other ear. Common FcR gamma-chain knockout mice are unable to express a functional high affinity receptor for IgE (FcεRI), and so injected IgE should have little or no effect in these animals.

12 hours later mice were injected intravenously with 200 µg of human serum albumin coupled to DNP (HSA DNP) in PBS containing 1% Evans blue. 45-60 minutes post injection edema formation was quantified by measuring the affected area of the ear (area of visible dye).

Figure 7:
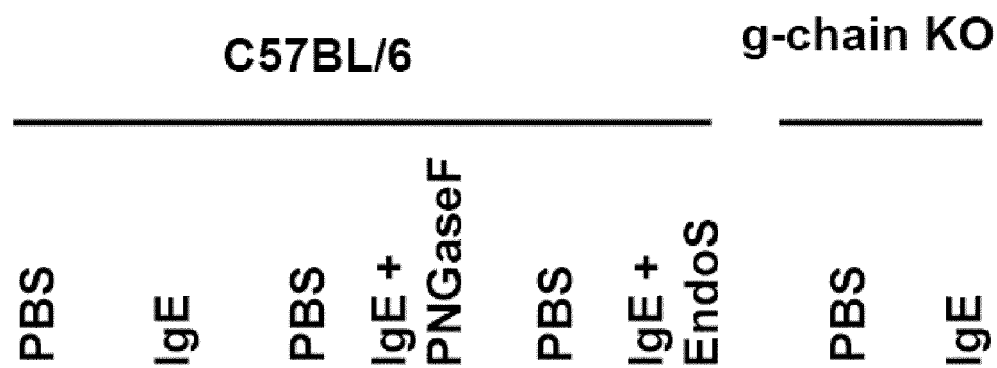
FIG. 7. EndoS treated IgE has reduced activity in vivo. Mouse IgE anti-DNP was treated with EndoS or PNGaseF. Untreated IgE, PNGaseF-treated IgE or EndoS-treated IgE was injected intradermally into one ear and PBS as a control into the other ear of C57BL/6 mice. FcR common gamma-chain knockout mice were used as a control, and received untreated IgE injected into one ear and PBS into the other ear. 12 hours later all mice were injected intravenously with human serum albumin coupled to DNP (HSA DNP) in PBS containing 1% Evans blue. 45-60 minutes post injection edema formation was quantified by measuring the affected area of the ear. A) Representative individuals of the experimental groups B) Quantification of the data. In C57BL/6 mice, all groups showed a significantly reduced edema size (p<0.005) compared to ears injected with untreated IgE.
Figure 7:
Figure 7:
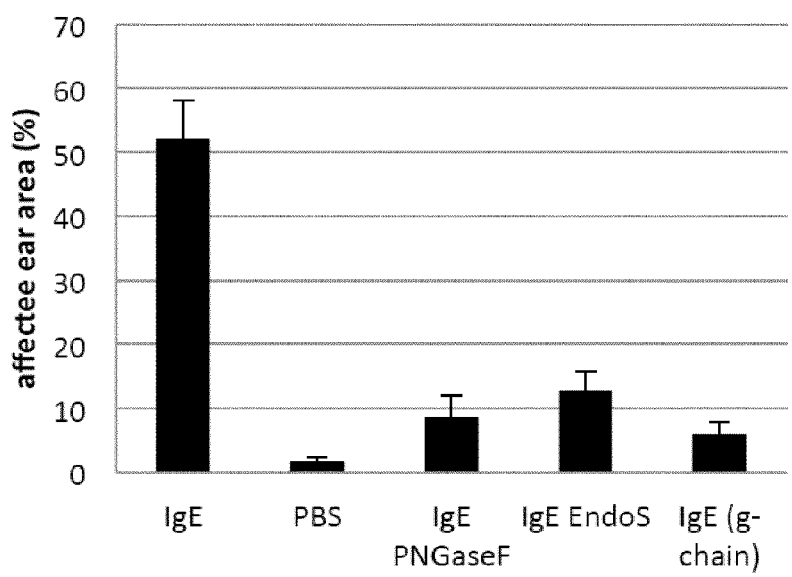

As shown in FIGS. 7A and 7B, for C57BL/6 mice, ears receiving PBS, PNGaseF-treated IgE or EndoS-treated IgE had significantly reduced edema size (p<0.005) relative to ears receiving untreated IgE. As expected, FCεRI gamma-chain knockout mice also had significantly lower edema size compared to C57BL/6 mice receiving untreated IgE, demonstrating that the observed edema is caused by IgE activity on cells.

Example 7

Administration of EndoS Inhibits IgE Activity In Vivo 20 ng anti-DNP IgE was injected intradermally into one ear and PBS as a control into the other ear of C57BL/6 mice. 3 and 8 hours later, either 100 µg EndoS (treatment) or PBS (control) was injected intravenously. 12 hours after IgE injection mice were injected intravenously with 200 µg of human serum albumin coupled to DNP (HSA DNP) in PBS containing 1% Evans blue. 45-60 minutes post injection edema formation was quantified by measuring the affected area of the ear (area of visible dye).

Figure 8A:
FIG. 8A shows representative animals. Upper mouse received PBS (control), lower mouse received EndoS (treatment).
Figure 8:
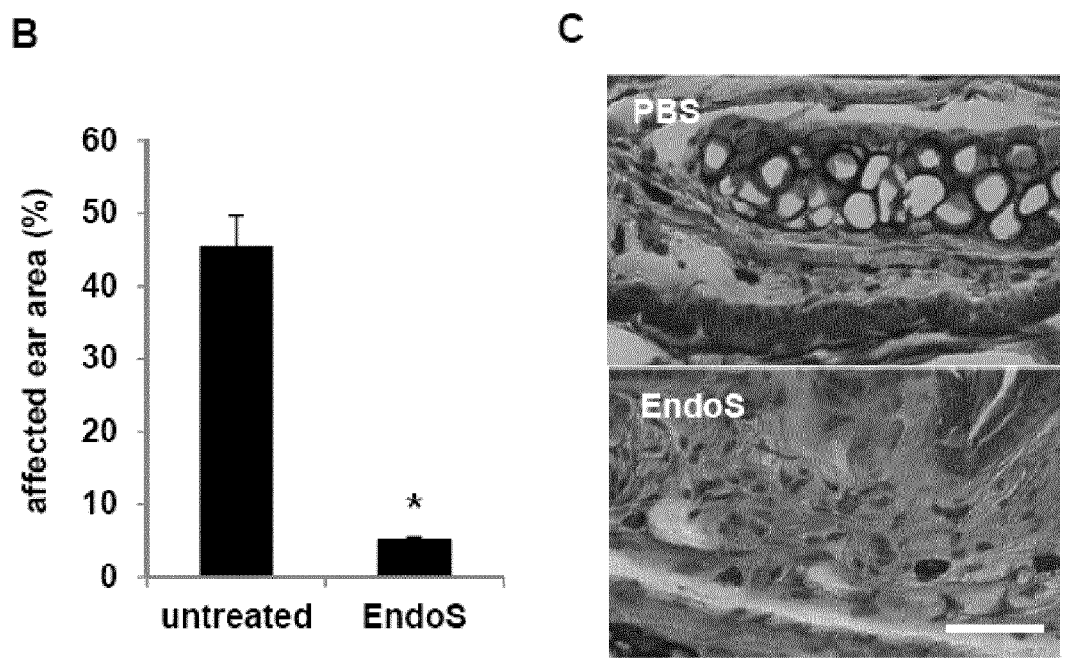
FIG. 8. Administration of EndoS reduces IgE activity in vivo. Anti-DNP IgE was injected intradermally into one ear and PBS as a control into the other ear of C57BL/6 mice. 3 and 8 hours later EndoS (treatment) or PBS (control) was injected intravenously. 12 hours after IgE injection mice were injected intravenously with human serum albumin coupled to DNP (HSA DNP) in PBS containing 1% Evans blue. 45-60 minutes post injection edema formation was quantified by measuring the affected area of the ear.
Figure 8:
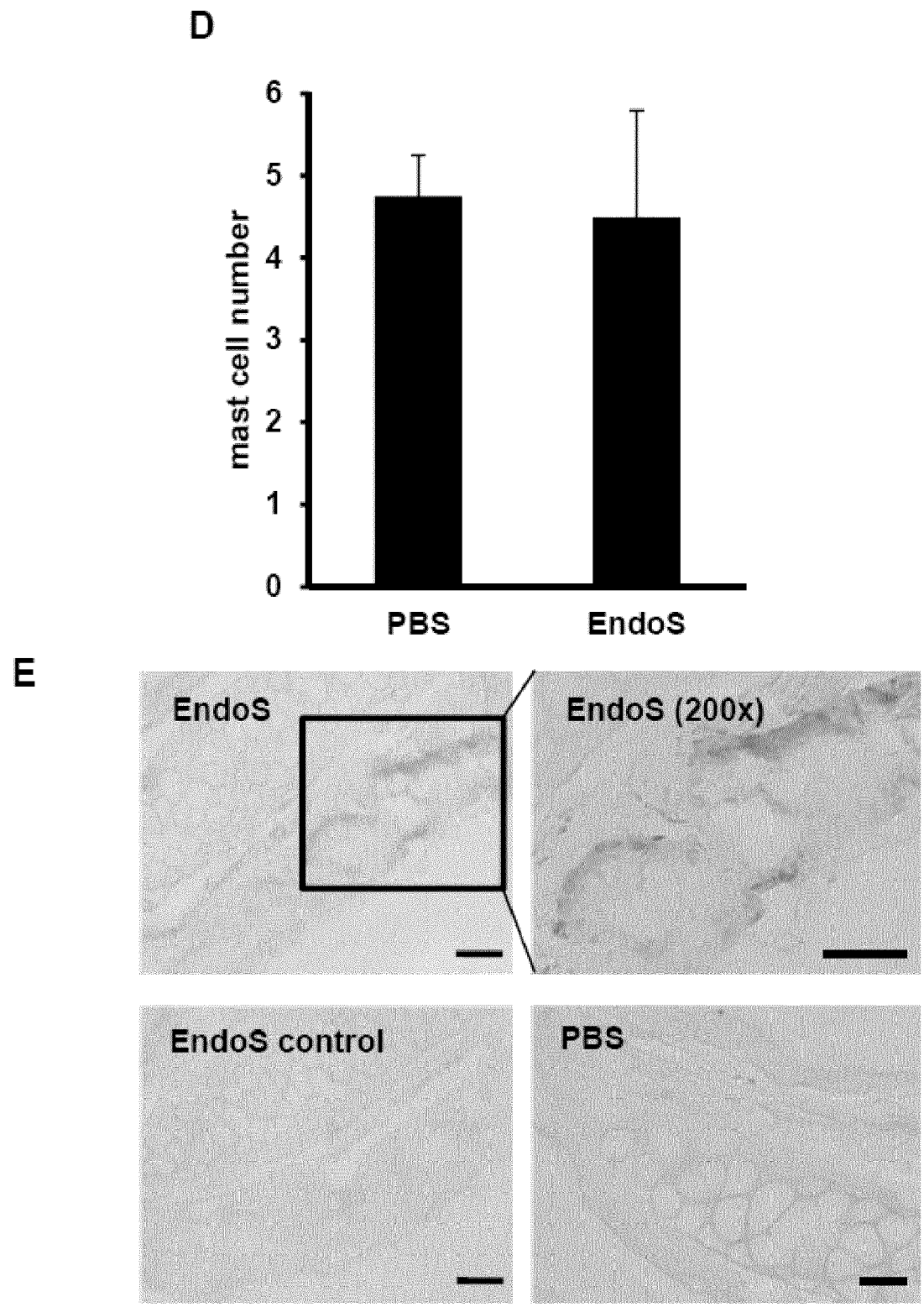

FIG. 8A shows representative animals: lower mouse received EndoS (treatment), upper mouse received PBS (control). The size of the affected area in each animal was measured and the results are shown in FIG. 8B. As is shown, animals receiving EndoS treatment had a significantly reduced size of affected area in the IgE treated ear, indicating that EndoS interferes with mast cell activation in vivo.

However, as shown in FIG. 8C and quantified in FIG. 8D, EndoS treatment does not result in a reduction of mast cells in the skin. Interestingly, FIG. 8E shows that EndoS can be detected in ear tissue with a polyclonal EndoS specific antibody, suggesting that intravenously injected EndoS has the capacity to leave the blood stream and reach peripheral tissues such as the skin.

The presence of mast cells and EndoS in the skin was investigated by histology. Ear tissue was removed, fixed in 10% buffered formalin, and embedded in paraffin. Six micrometer paraffin sections were cut, dried overnight and stained with toluidine blue (Sigma, Steinheim, Germany) to detect mast cells or with a polyclonal EndoS specific antibody followed by detection with a secondary horseradish peroxidase (HRP) coupled antibody to detect EndoS (Jackson Immunoresearch, Newmarket, UK).

Example 8

Further Analysis of Reduced In Vivo Activity of IgE Treated In Vitro with Endos

To further analyse the effects of PNGaseF and EndoS treatment on IgE dependent mast cell activation, further reverse passive cutaneous anaphylaxis experiments were carried out as in Example 6, comparing the effects of untreated anti-DNP IgE, anti-DNP IgE pre-treated with EndoS, and anti-DNP IgE pre-treated with PNGaseF.

Figure 9:
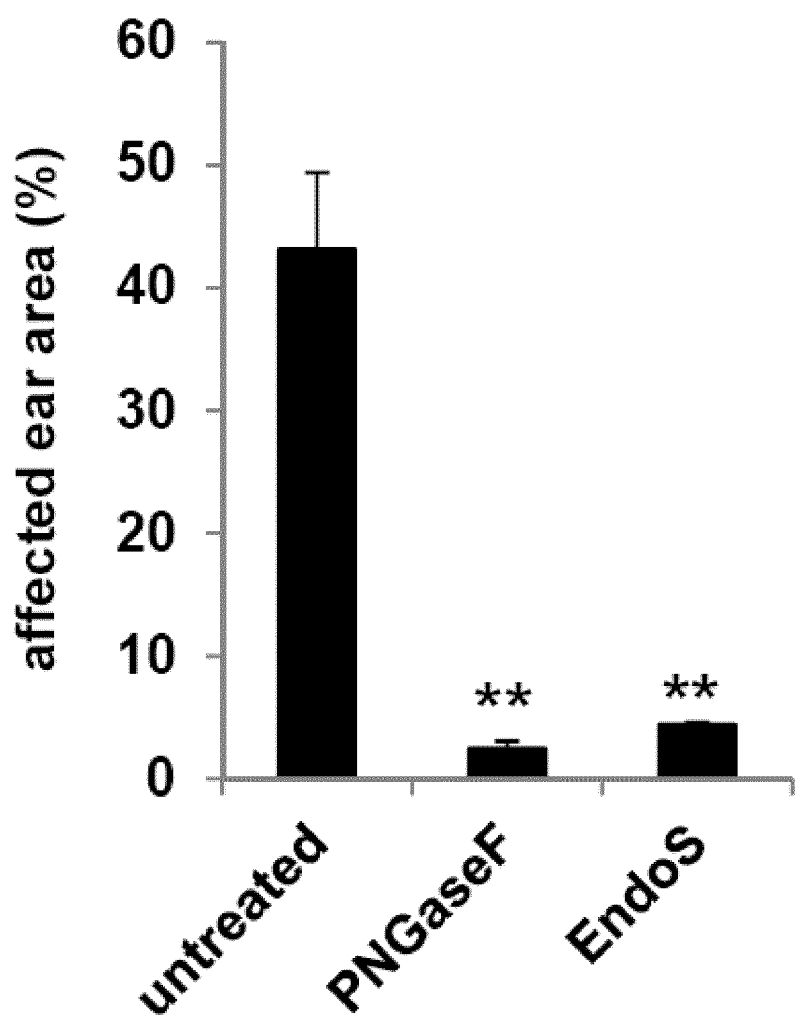
FIG. 9. EndoS treated IgE has reduced activity in vivo.

As shown in FIG. 9, treatment by either EndoS or PNGaseF results in a highly significant reduction in the capacity of IgE to induce edema formation. Students t-test was used to evaluate statistical significance and a p-value <0.05 was considered significant.

The invention claimed is:

1. A method of treating a disease or condition mediated by pathogenic IgE antibodies in a subject, the method comprising:
   (a) selecting a subject having a disease or condition characterized by one or more of (i) undesirable IgE production, (ii) excessive, harmful or unwanted IgE-mediated basophil activation, and (iii) excessive, harmful or unwanted IgE-mediated mast cell activation, wherein the disease or condition is selected from a hyper-IgE syndrome, an atopic disorder, an allergic reaction, and a hypersensitivity reaction characterized by having an abnormally increased amount of IgE specific for one or more allergens; and
   (b) administering to the subject a therapeutically effective amount of an EndoS polypeptide to reduce interactions between the pathogenic IgE antibodies and FcεR on FcεR bearing cells in the subject, relative to said interactions prior to said step of administering, and thereby treating the disease or condition mediated by pathogenic IgE antibodies,
   wherein the EndoS polypeptide comprises:
   (i) the amino acid sequence of SEQ ID NO: 1,
   (ii) a fragment of (i) having IgE endoglycosidase activity which hydrolyzes at least one IgE Cε asparagine-linked glycan between two core N-acetylglucosamine residues of the glycan,
   (iii) a variant of (i) having at least 97% identity to the amino acid sequence of SEQ ID NO: 1 and having IgE endoglycosidase activity which hydrolyzes at least one IgE Cε asparagine-linked glycan between two core N-acetylglucosamine residues of the glycan; or
   (iv) a variant of (ii) having at least 97% identity to a corresponding portion of the amino acid sequence of SEQ ID NO: 1 and having IgE endoglycosidase activity which hydrolyzes at least one IgE Cε asparagine-linked glycan between two core N-acetylglucosamine residues of the glycan.

2. The method of claim 1 wherein said EndoS polypeptide consists of the amino acid sequence of SEQ ID NO: 1.

3. The method of claim 1, wherein said disease or condition is characterized by presence of at least one symptom selected from atopic dermatitis, allergic rhinitis, allergic conjunctivitis and allergic asthma.

4. The method of claim 1, wherein said atopic disorder or allergic or hypersensitivity reaction is characterized by an immune response to a plant allergen, an animal dander allergen, a mold or fungal allergen, a dust allergen, a dust mite allergen, a stinging insect venom, an environmental allergen, a food allergen or a therapeutic agent.

5. The method of claim 4 wherein said immune response is a response to at least one of: cat dander protein Fel d1; House dust mite proteins Der P1, Der P2 and Der P7; Ragweed protein amb a 1.1, a 1.2, a1.3 or a1.4; Rye grass proteins lol p1and lol p5; Timothy grass proteins phl p1 and phl p5; Bermuda grass protein Cyn d 5; Alternaria alternate proteins Alt a 1, Alt a 2 and Enolase (Alt a 6); Birch protein Bet v1and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut protein Ara h1, Ara h2, Ara h3, Ara h4, Ara H5, Ara h6, a plant profilin; a lipid transfer protein; an antibiotic; and an anti-cancer agent.

6. The method of claim 4 wherein the plant allergen is a grass allergen.

* * * * *

UNITED STATES PATENT AND TRADEMARK OFFICE
CERTIFICATE OF CORRECTION

PATENT NO. : 9,707,279 B2
APPLICATION NO. : 14/002949
DATED : July 18, 2017
INVENTOR(S) : Mattias Collins et al.

Page 1 of 1

It is certified that error appears in the above-identified patent and that said Letters Patent is hereby corrected as shown below:

In the Claims

Column 38, Line 57:
"Bet v1and PI4; German Cockroach proteins Bla g 1, Bla g"
Should read:
--Bet v1 and PI4; German Cockroach proteins Bla g 1, Bla g--.

Column 38, Line 60:
"protein Ara h1, Ara h2, Ara h3, Ara h4, Ara H5, Ara h6, a"
Should read:
--protein Ara h1, Ara h2, Ara h3, Ara h4, Ara h5, Ara h6, a--.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 3

<210> SEQ ID NO 1
<211> LENGTH: 959
<212> TYPE: PRT
<213> ORGANISM: Streptococcus pyogenes

<400> SEQUENCE: 1

```
Glu Glu Lys Thr Val Gln Val Gln Lys Gly Leu Pro Ser Ile Asp Ser
1               5                   10                  15

Leu His Tyr Leu Ser Glu Asn Ser Lys Glu Phe Lys Glu Glu Leu
            20                  25                  30

Ser Lys Ala Gly Gln Glu Ser Gln Lys Val Lys Glu Ile Leu Ala Lys
            35                  40                  45

Ala Gln Gln Ala Asp Lys Gln Ala Gln Glu Leu Ala Lys Met Lys Ile
        50                  55                  60

Pro Glu Lys Ile Pro Met Lys Pro Leu His Gly Pro Leu Tyr Gly Gly
65                  70                  75                  80

Tyr Phe Arg Thr Trp His Asp Lys Thr Ser Asp Pro Thr Glu Lys Asp
                85                  90                  95

Lys Val Asn Ser Met Gly Glu Leu Pro Lys Glu Val Asp Leu Ala Phe
                100                 105                 110

Ile Phe His Asp Trp Thr Lys Asp Tyr Ser Leu Phe Trp Lys Glu Leu
            115                 120                 125

Ala Thr Lys His Val Pro Lys Leu Asn Lys Gln Gly Thr Arg Val Ile
        130                 135                 140

Arg Thr Ile Pro Trp Arg Phe Leu Ala Gly Gly Asp Asn Ser Gly Ile
145                 150                 155                 160

Ala Glu Asp Thr Ser Lys Tyr Pro Asn Thr Pro Glu Gly Asn Lys Ala
                165                 170                 175

Leu Ala Lys Ala Ile Val Asp Glu Tyr Val Tyr Lys Tyr Asn Leu Asp
            180                 185                 190

Gly Leu Asp Val Asp Val Glu His Asp Ser Ile Pro Lys Val Asp Lys
        195                 200                 205

Lys Glu Asp Thr Ala Gly Val Glu Arg Ser Ile Gln Val Phe Glu Glu
    210                 215                 220

Ile Gly Lys Leu Ile Gly Pro Lys Gly Val Asp Lys Ser Arg Leu Phe
225                 230                 235                 240

Ile Met Asp Ser Thr Tyr Met Ala Asp Lys Asn Pro Leu Ile Glu Arg
                245                 250                 255

Gly Ala Pro Tyr Ile Asn Leu Leu Leu Val Gln Val Tyr Gly Ser Gln
            260                 265                 270

Gly Glu Lys Gly Gly Trp Glu Pro Val Ser Asn Arg Pro Glu Lys Thr
        275                 280                 285

Met Glu Glu Arg Trp Gln Gly Tyr Ser Lys Tyr Ile Arg Pro Glu Gln
    290                 295                 300

Tyr Met Ile Gly Phe Ser Phe Tyr Glu Glu Asn Ala Gln Glu Gly Asn
305                 310                 315                 320

Leu Trp Tyr Asp Ile Asn Ser Arg Lys Asp Glu Asp Lys Ala Asn Gly
                325                 330                 335

Ile Asn Thr Asp Ile Thr Gly Thr Arg Ala Glu Arg Tyr Ala Arg Trp
            340                 345                 350

Gln Pro Lys Thr Gly Gly Val Lys Gly Gly Ile Phe Ser Tyr Ala Ile
        355                 360                 365
```

-continued

Asp Arg Asp Gly Val Ala His Gln Pro Lys Lys Tyr Ala Lys Gln Lys
370             375                 380

Glu Phe Lys Asp Ala Thr Asp Asn Ile Phe His Ser Asp Tyr Ser Val
385             390                 395                 400

Ser Lys Ala Leu Lys Thr Val Met Leu Lys Asp Lys Ser Tyr Asp Leu
            405                 410                 415

Ile Asp Glu Lys Asp Phe Pro Asp Lys Ala Leu Arg Glu Ala Val Met
            420                 425                 430

Ala Gln Val Gly Thr Arg Lys Gly Asp Leu Glu Arg Phe Asn Gly Thr
                435                 440                 445

Leu Arg Leu Asp Asn Pro Ala Ile Gln Ser Leu Glu Gly Leu Asn Lys
450                 455                 460

Phe Lys Lys Leu Ala Gln Leu Asp Leu Ile Gly Leu Ser Arg Ile Thr
465                 470                 475                 480

Lys Leu Asp Arg Ser Val Leu Pro Ala Asn Met Lys Pro Gly Lys Asp
                485                 490                 495

Thr Leu Glu Thr Val Leu Glu Thr Tyr Lys Lys Asp Asn Lys Glu Glu
                500                 505                 510

Pro Ala Thr Ile Pro Pro Val Ser Leu Lys Val Ser Gly Leu Thr Gly
                515                 520                 525

Leu Lys Glu Leu Asp Leu Ser Gly Phe Asp Arg Glu Thr Leu Ala Gly
530                 535                 540

Leu Asp Ala Ala Thr Leu Thr Ser Leu Glu Lys Val Asp Ile Ser Gly
545                 550                 555                 560

Asn Lys Leu Asp Leu Ala Pro Gly Thr Glu Asn Arg Gln Ile Phe Asp
                565                 570                 575

Thr Met Leu Ser Thr Ile Ser Asn His Val Gly Ser Asn Glu Gln Thr
                580                 585                 590

Val Lys Phe Asp Lys Gln Lys Pro Thr Gly His Tyr Pro Asp Thr Tyr
                595                 600                 605

Gly Lys Thr Ser Leu Arg Leu Pro Val Ala Asn Glu Lys Val Asp Leu
610                 615                 620

Gln Ser Gln Leu Leu Phe Gly Thr Val Thr Asn Gln Gly Thr Leu Ile
625                 630                 635                 640

Asn Ser Glu Ala Asp Tyr Lys Ala Tyr Gln Asn His Lys Ile Ala Gly
                645                 650                 655

Arg Ser Phe Val Asp Ser Asn Tyr His Tyr Asn Asn Phe Lys Val Ser
                660                 665                 670

Tyr Glu Asn Tyr Thr Val Lys Val Thr Asp Ser Thr Leu Gly Thr Thr
                675                 680                 685

Thr Asp Lys Thr Leu Ala Thr Asp Lys Glu Glu Thr Tyr Lys Val Asp
690                 695                 700

Phe Phe Ser Pro Ala Asp Lys Thr Lys Ala Val His Thr Ala Lys Val
705                 710                 715                 720

Ile Val Gly Asp Glu Lys Thr Met Met Val Asn Leu Ala Glu Gly Ala
                725                 730                 735

Thr Val Ile Gly Gly Ser Ala Asp Pro Val Asn Ala Arg Lys Val Phe
                740                 745                 750

Asp Gly Gln Leu Gly Ser Glu Thr Asp Asn Ile Ser Leu Gly Trp Asp
                755                 760                 765

Ser Lys Gln Ser Ile Ile Phe Lys Leu Lys Glu Asp Gly Leu Ile Lys
770                 775                 780

His Trp Arg Phe Phe Asn Asp Ser Ala Arg Asn Pro Glu Thr Thr Asn

```
785                 790                 795                 800
Lys Pro Ile Gln Glu Ala Ser Leu Gln Ile Phe Asn Ile Lys Asp Tyr
                805                 810                 815

Asn Leu Asp Asn Leu Leu Glu Asn Pro Asn Lys Phe Asp Asp Glu Lys
                820                 825                 830

Tyr Trp Ile Thr Val Asp Thr Tyr Ser Ala Gln Gly Glu Arg Ala Thr
                835                 840                 845

Ala Phe Ser Asn Thr Leu Asn Asn Ile Thr Ser Lys Tyr Trp Arg Val
        850                 855                 860

Val Phe Asp Thr Lys Gly Asp Arg Tyr Ser Ser Pro Val Val Pro Glu
865                 870                 875                 880

Leu Gln Ile Leu Gly Tyr Pro Leu Pro Asn Ala Asp Thr Ile Met Lys
                885                 890                 895

Thr Val Thr Thr Ala Lys Glu Leu Ser Gln Gln Lys Asp Lys Phe Ser
                900                 905                 910

Gln Lys Met Leu Asp Glu Leu Lys Ile Lys Glu Met Ala Leu Glu Thr
                915                 920                 925

Ser Leu Asn Ser Lys Ile Phe Asp Val Thr Ala Ile Asn Ala Asn Ala
        930                 935                 940

Gly Val Leu Lys Asp Cys Ile Glu Lys Arg Gln Leu Leu Lys Lys
945                 950                 955

<210> SEQ ID NO 2
<211> LENGTH: 995
<212> TYPE: PRT
<213> ORGANISM: Streptococcus pyogenes

<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65              70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Thr Ser Lys Tyr Pro Asn Thr Pro Glu
        195                 200                 205
```

```
Gly Asn Lys Ala Leu Ala Lys Ala Ile Val Asp Glu Tyr Val Tyr Lys
    210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
                340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
            405                 410                 415

Ala Lys Gln Lys Glu Phe Lys Asp Ala Thr Asp Asn Ile Phe His Ser
        420                 425                 430

Asp Tyr Ser Val Ser Lys Ala Leu Lys Thr Val Met Leu Lys Asp Lys
    435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
```

-continued

```
                625                 630                 635                 640
        Pro Asp Thr Tyr Gly Lys Thr Ser Leu Arg Leu Pro Val Ala Asn Glu
                            645                 650                 655
        Lys Val Asp Leu Gln Ser Gln Leu Leu Phe Gly Thr Val Thr Asn Gln
                            660                 665                 670
        Gly Thr Leu Ile Asn Ser Glu Ala Asp Tyr Lys Ala Tyr Gln Asn His
                            675                 680                 685
        Lys Ile Ala Gly Arg Ser Phe Val Asp Ser Asn Tyr His Tyr Asn Asn
                            690                 695                 700
        Phe Lys Val Ser Tyr Glu Asn Tyr Thr Val Lys Val Thr Asp Ser Thr
        705                 710                 715                 720
        Leu Gly Thr Thr Thr Asp Lys Thr Leu Ala Thr Asp Lys Glu Glu Thr
                            725                 730                 735
        Tyr Lys Val Asp Phe Phe Ser Pro Ala Asp Lys Thr Lys Ala Val His
                            740                 745                 750
        Thr Ala Lys Val Ile Val Gly Asp Glu Lys Thr Met Met Val Asn Leu
                            755                 760                 765
        Ala Glu Gly Ala Thr Val Ile Gly Gly Ser Ala Asp Pro Val Asn Ala
                            770                 775                 780
        Arg Lys Val Phe Asp Gly Gln Leu Gly Ser Glu Thr Asp Asn Ile Ser
        785                 790                 795                 800
        Leu Gly Trp Asp Ser Lys Gln Ser Ile Ile Phe Lys Leu Lys Glu Asp
                            805                 810                 815
        Gly Leu Ile Lys His Trp Arg Phe Phe Asn Asp Ser Ala Arg Asn Pro
                            820                 825                 830
        Glu Thr Thr Asn Lys Pro Ile Gln Glu Ala Ser Leu Gln Ile Phe Asn
                            835                 840                 845
        Ile Lys Asp Tyr Asn Leu Asp Asn Leu Leu Glu Asn Pro Asn Lys Phe
                            850                 855                 860
        Asp Asp Glu Lys Tyr Trp Ile Thr Val Asp Thr Tyr Ser Ala Gln Gly
        865                 870                 875                 880
        Glu Arg Ala Thr Ala Phe Ser Asn Thr Leu Asn Asn Ile Thr Ser Lys
                            885                 890                 895
        Tyr Trp Arg Val Val Phe Asp Thr Lys Gly Asp Arg Tyr Ser Ser Pro
                            900                 905                 910
        Val Val Pro Glu Leu Gln Ile Leu Gly Tyr Pro Leu Pro Asn Ala Asp
                            915                 920                 925
        Thr Ile Met Lys Thr Val Thr Thr Ala Lys Glu Leu Ser Gln Gln Lys
                            930                 935                 940
        Asp Lys Phe Ser Gln Lys Met Leu Asp Glu Leu Lys Ile Lys Glu Met
        945                 950                 955                 960
        Ala Leu Glu Thr Ser Leu Asn Ser Lys Ile Phe Asp Val Thr Ala Ile
                            965                 970                 975
        Asn Ala Asn Ala Gly Val Leu Lys Asp Cys Ile Glu Lys Arg Gln Leu
                            980                 985                 990
        Leu Lys Lys
                995

<210> SEQ ID NO 3
<211> LENGTH: 3403
<212> TYPE: DNA
<213> ORGANISM: Streptococcus pyogenes

<400> SEQUENCE: 3
```

-continued

```
ctcttttgtc ctgccatgga tggcaggttg gcaaaaaaat gagaaaagcc taaaaacctt      60
aaatttgtgt tattttacct atactttgta ccttgttttt tttaataaag tgttgttata     120
cttaaggcga actataggaa tgcgcttaca tggatggtat atcaactggg aagccatgac     180
ttagtaccaa aaataaggag tgtccaaatg gataaacatt tgttggtaaa agaacacta      240
gggtgtgttt gtgctgcaac gttgatggga gctgccttag cgacccacca tgattcactc     300
aatactgtaa aagcggagga gaagactgtt caggttcaga aaggattacc ttctatcgat     360
agcttgcatt atctgtcaga gaatagcaaa aagaattta aagaagaact ctcaaaagcg      420
gggcaagaat ctcaaaaggt caaagagata ttagcaaaag ctcagcaggc agataaacaa     480
gctcaagaac ttgccaaaat gaaaattcct gagaaaatac cgatgaaacc gttacatggt     540
cctctctacg gtggttactt tagaacttgg catgacaaaa catcagatcc aacagaaaaa     600
gacaaagtta actcgatggg agagcttcct aaagaagtag atctagcctt tattttccac     660
gattggacaa aagattatag cctttttggg aaagaattgg ccaccaaaca tgtgccaaag     720
ttaaacaagc aagggacacg tgtcattcgt accattccat ggcgtttcct agctgggggt     780
gataacagtg gtattgcaga agataccagt aaatacccaa atacaccaga gggaaataaa     840
gctttagcca aagctattgt tgatgaatat gtttataaat acaaccttga tggcttagat     900
gtggatgttg aacatgatag tattccaaaa gttgacaaaa aagaagatac agcaggcgta     960
gaacgctcta ttcaagtgtt tgaagaaatt gggaaattaa ttggaccaaa aggtgttgat    1020
aaatcgcggt tatttattat ggatagcacc tacatggctg ataaaaaccc attgattgag    1080
cgaggagctc cttatattaa tttattactg gtacaggtct atggttcaca aggagagaaa    1140
ggtggttggg agcctgtttc taatcgacct gaaaaaacaa tggaagaacg atggcaaggt    1200
tatagcaagt atattcgtcc tgaacaatac atgattggtt tttctttcta tgaggaaaat    1260
gctcaagaag ggaatctttg gtatgatatt aattctcgca aggacgagga caaagcaaat    1320
ggaattaaca ctgacataac tggaacgcgt gccgaacggt atgcaaggtg caacctaag     1380
acaggtgggg ttaagggagg tatcttctcc tacgctattg accgagatgg tgtagctcat    1440
caacctaaaa aatatgctaa acagaaagag tttaaggacg caactgataa catcttccac    1500
tcagattata gtgtctccaa ggcattaaag acagttatgc taaagataa gtcgtatgat    1560
ctgattgatg agaaagattt cccagataag gctttgcgag aagctgtgat ggcgcaggtt    1620
ggaaccagaa aaggtgattt ggaacgtttc aatggcacat tacgattgga taatccagcg    1680
attcaaagtt tagaaggtct aaataaattt aaaaaattag ctcaattaga cttgattggc    1740
ttatctcgca ttacaaagct cgaccgttct gttttacccg ctaatatgaa gccaggcaaa    1800
gataccttgg aaacagttct tgaaacctat aaaaaggata caaagaaga acctgctact    1860
atcccaccag tatctttgaa ggtttctggt ttaactggtc tgaaagaatt agatttgtca    1920
ggttttgacc gtgaaacctt ggctggtctt gatgccgcta ctctaacgtc tttagaaaaa    1980
gttgatattt ctggcaacaa acttgatttg gctccaggaa cagaaaatcg acaaattttt    2040
gatactatgc tatcaactat cagcaatcat gttggaagca atgaacaaac agtgaaattt    2100
gacaagcaaa aaccaactgg gcattaccca gataccatg ggaaaactag tctgcgctta    2160
ccagtggcaa atgaaaaagt tgatttgcaa agccagcttt tgtttgggac tgtgacaaat    2220
caaggaaccc taatcaatag cgaagcagac tataaggctt accaaaatca taaaattgct    2280
ggacgtagct ttgttgattc aaactatcat tacaataact ttaaagtttc ttatgagaac    2340
tataccgtta aagtaactga ttccacattg gaaccacta ctgacaaaac gctagcaact    2400
```

```
gataaagaag agacctataa ggttgacttc tttagcccag cagataagac aaaagctgtt    2460
catactgcta aagtgattgt tggtgacgaa aaaaccatga tggttaattt ggcagaaggc    2520
gcaacagtta ttggaggaag tgctgatcct gtaaatgcaa gaaaggtatt tgatgggcaa    2580
ctgggcagtg agactgataa tatctcttta ggatgggatt ctaagcaaag tattatattt    2640
aaattgaaag aagatggatt aataaagcat tggcgtttct tcaatgattc agcccgaaat    2700
cctgagacaa ccaataaacc tattcaggaa gcaagtctac aaattttaa tatcaaagat     2760 tataatctag ataatttgtt ggaaaatccc aataaatttg atgatgaaaa atattggatt    2820
actgtagata cttacagtgc acaaggagag agagctactg cattcagtaa tacattaaat    2880
aatattacta gtaaatattg gcgagttgtc tttgatacta aaggagatag atatagttcg    2940
ccagtagtcc ctgaactcca aatttttaggt tatccgttac ctaacgccga cactatcatg   3000
aaaacagtaa ctactgctaa agagttatct caacaaaaag ataagttttc tcaaaagatg    3060
cttgatgagt taaaaataaa agagatggct ttagaaactt cttgaacag taagattttt     3120 gatgtaactg ctattaatgc taatgctgga gttttgaaag attgtattga gaaaaggcag    3180
ctgctaaaaa aataaacaaa gtaactttct tagatagcaa cattcagatt aaattaacaa    3240
aatgtgacta tgataaaggt ttgctggaat tgattaacca aaagactaaa aatctgagat    3300
gaatagtccc agatttttag tcttttatag gttttgatga cataaagcta aataatcgtt    3360
agactaccag aaagggcgct tgtccgtgag acatggctgt ctt                      3403
```